(12) United States Patent
Douin et al.

(10) Patent No.: US 8,114,389 B2
(45) Date of Patent: Feb. 14, 2012

(54) NANOEMULSIONS COMPRISING AT LEAST ONE AMPHIPHILIC LIPID, AT LEAST ONE OIL, AND AT LEAST ONE NONIONIC POLYMER, AND USES THEREOF

(75) Inventors: Véronique Douin, Paris (FR); Bénédicte Cazin, Clichy (FR); Jean-Thierry Simonnet, Paris (FR); Odile Aubrun, Paris (FR)

(73) Assignee: L'Oreal S.A., Paris (FR)

( * ) Notice: Subject to any disclaimer, the term of this patent is extended or adjusted under 35 U.S.C. 154(b) by 1319 days.

(21) Appl. No.: 11/097,371

(22) Filed: Apr. 4, 2005

(65) Prior Publication Data

US 2005/0226842 A1    Oct. 13, 2005

Related U.S. Application Data

(63) Continuation of application No. 09/766,403, filed on Jan. 22, 2001, now abandoned.

(30) Foreign Application Priority Data

Jan. 21, 2000 (FR) ..................... 00 00793

(51) Int. Cl.
*A61K 8/06* (2006.01)
*A61K 8/02* (2006.01)

(52) U.S. Cl. ............... 424/70.1; 424/401; 424/70.11; 424/70.27; 424/70.28; 424/70.22

(58) Field of Classification Search .............. 424/70.1, 424/401, 70.11, 70.27, 70.28
See application file for complete search history.

(56) References Cited

U.S. PATENT DOCUMENTS

| | | | |
|---|---|---|---|
| 4,137,180 A | 1/1979 | Naik et al. | |
| 4,155,892 A * | 5/1979 | Emmons et al. | 524/507 |
| 4,185,087 A | 1/1980 | Morlino | |
| 4,788,001 A | 11/1988 | Narula | |
| 4,874,554 A | 10/1989 | Lange et al. | |
| 5,135,748 A | 8/1992 | Ziegler et al. | |
| 5,152,923 A | 10/1992 | Weder et al. | |
| 5,246,693 A | 9/1993 | Grollier et al. | |
| 5,364,633 A | 11/1994 | Hill | |
| 5,411,744 A | 5/1995 | Hill et al. | |
| 5,426,182 A | 6/1995 | Jenkins et al. | |
| 5,716,418 A | 2/1998 | Matzik et al. | |
| 5,753,241 A | 5/1998 | Ribier et al. | |
| 5,925,341 A * | 7/1999 | Cervantes et al. | 424/78.03 |
| 6,039,936 A | 3/2000 | Restle et al. | |
| 6,120,757 A | 9/2000 | Dubief et al. | |
| 6,120,778 A | 9/2000 | Simonnet | |
| 6,468,551 B1 | 10/2002 | Diec et al. | |
| 6,488,780 B2 | 12/2002 | Cauwet-Martin | |
| 6,533,873 B1 | 3/2003 | Margosiak et al. | |
| 6,562,356 B2 | 5/2003 | Verite et al. | |
| 6,607,733 B1 | 8/2003 | Diec et al. | |
| 2005/0226842 A1 | 10/2005 | Douin et al. | |

FOREIGN PATENT DOCUMENTS

| | | |
|---|---|---|
| EP | 0 095 238 | 11/1983 |
| EP | 0 107 199 | 5/1984 |
| EP | 0 270 249 | 6/1988 |
| EP | 406 162 A2 | 1/1991 |
| EP | 0 455 185 | 11/1991 |
| EP | 0 530 974 | 3/1993 |
| EP | 0 728 460 | 8/1996 |
| EP | 0 780 114 | 6/1997 |
| EP | 0 814 753 B1 | 1/1998 |
| EP | 0 842 652 | 5/1998 |
| EP | 0 879 589 | 11/1998 |
| EP | 1 120 102 B1 | 8/2001 |
| GB | 2 131 820 | 6/1984 |
| JP | 10338899 | 12/1998 |
| WO | WO 94/00508 | 6/1994 |
| WO | WO 96/28132 A2 | 9/1996 |
| WO | WO 98/15255 A1 | 4/1998 |
| WO | WO 98/22087 A1 | 5/1998 |
| WO | WO 9936047 A1 * | 7/1999 |
| WO | WO 99/53889 | 10/1999 |
| WO | WO 99/56703 | 11/1999 |

OTHER PUBLICATIONS

English language Derwent Abstract of EP 0 879 589.
Becher, *Dictionary of Colloid and Surface Science*, Marcel Dekker, Inc., New York, p. 100-103 (1990).
Bourrel et al., *Microemulsion and related systems*, Marcel Dekker, Inc., New York, p. 24-30, 460-462 (1988).
Clarke, Ch. 4 Rheological Additives, in Rheological Properties of Cosmetics and Toiletries, ed. by D. Laba, Marcel Dekker, Inc., New York, p. 55-56, 94-97 and 110-118 (1993).
Decostelle et al. Washing cosmetic product composition and use of the same, English translation of JP H10-338899 (Decoster et al.).
Falbe et al., Stichwort "1-Hexadecanol,"*Römpp Chemie Lexikon*, 9. Auflage, Band 3, Georg Thieme Verlag Stuttgart, New York, p. 1793 (1995).
Forgiarini et al., "Comité espagnol de la detergence, tensioactivos y afines," p. 73-74 (1999). Abstract.
Forgiarini et al., "Studies of the relation between phase behavior and emulsification methods with nanoemulsion formation," *Progr. Colloid Polym. Sci.*, 115: 36-39 (2000).
Gottschalck et al., *International Cosmetic Ingredient Dictionary and Handbook*, 10th Ed., vol. 2, The Cosmetic, Toiletry, and Fragrance Association, Monographs 1365-1366 (2004).
Gradzielski et al.,"Hydrophobically cross-linked micellar solutions: microstructure and properties of the soluctions," *Journal de Physique IV*, Supplement au Journal de Physique II, vol. 3, p. 65-79 (1993).
Hoffman et al., Mikrostrukturen und Fliessverhalten viskoelastischer Tensidloesungen, *Nachr. Chem. Tech. Lab.*, 43(1): 9-14,16, 18 (1995).

(Continued)

*Primary Examiner* — Gina C Yu

(74) *Attorney, Agent, or Firm* — Finnegan, Henderson, Farabow, Garrett & Dunner, LLP

(57) ABSTRACT

Oil-in-water nanoemulsions comprising oil globules with an average size of less than 150 nm and comprising at least one oil, at least one amphiphilc lipid, and at least one nonionic polymer comprising at least one hydrophobic block and at least one hydrophilic block. Processes comprising such oil-in-water nanoemulsions.

74 Claims, No Drawings

OTHER PUBLICATIONS

Knowlton, "Emulsion Theory," *Poucher's Perfumes*, Cosmetics and Soaps, vol. 3, (1993, 9th ed. Hilda Butler), p. 552.

Le Hir, Abrégé de Pharmacie Galénique, 3éme Ed., 119-125, 132-133 (1981).

Restle et al. "Nonionic and cationic amphiphilic lipid-based nanoemulsion and its use," English translation of EP 0842652 A1.

Schrader, *Grundlagen and Rezepturen der Kosmetika*, Huthig Buch Verlag Heidelberg, Germany, p. 340-341 (1989).

Wenninger et al., *International Cosmetic Ingredient Dictionary*, $6^{th}$ Ed., vol. 1, The Cosmetic, Toiletry, and Fragrance Association, Monographs 753 (1995).

Wenninger et al., Cetyl Hydroxyethylcellulose, *International Cosmetic Ingredient Dictionary and Handbook*, 7th Ed., vol. 1, The Cosmetic, Toiletry, and Fragrance Association, Monographs 237 (1997).

Wenninger et al., *International Cosmetic Ingredient Dictionary and Handbook*, 7th Ed., vol. 2, The Cosmetic, Toiletry, and Fragrance Association, Monographs 1497 (1997).

Zulli et al., "Cationic Nanoparticles: A New System for the Delivery of Lipophilic UV-filters to Hair," *Drug & Cosmetic Industry Industry*, Apr. 1996, pp. 46-48.

Material Safety Data Sheet—Eusolex® 232 UV Filter (Ensulizole).

English translation of Auteur Inconnu: "Nephelometric Turbidity Unit" Wikipedia-Die Freie Enzyklopadie, pp. 1-2, Extrait de l'Internet le Apr. 5, 2009, http://de.wikipedia.org/wiki/Nephelometric_Turbidity_Unit.

Abandoned U.S. Appl. No. 09/765,675, filed Jan. 22, 2001.

* cited by examiner

NANOEMULSIONS COMPRISING AT LEAST ONE AMPHIPHILIC LIPID, AT LEAST ONE OIL, AND AT LEAST ONE NONIONIC POLYMER, AND USES THEREOF

This is a continuation of application Ser. No. 09/766,403, filed Jan. 22, 2001 now abandoned, which is incorporated herein by reference.

The present invention relates to O/W (oil-in-water) nanoemulsions comprising oil globules with an average size of less than 150 nm comprising at least one oil, at least one amphiphilc lipid, and at least one nonionic polymer comprising at least one hydrophobic block and at least one hydrophilic block. The present invention also relates to the use of such nanoemulsions in topical application, for example, in cosmetics and/or in dermopharmacy.

The term "nanoemulsion" means a metastable oil-in-water emulsion (wherein, for example, the emulsion can comprise an oily phase dispersed in an aqueous phase) whose oil globule size is less than 150 nm, these oil globules being stabilized with a crown of amphiphilic lipids which can optionally form a liquid crystal phase of lamellar type located at the oil/aqueous phase interface. The transparency of these emulsions derives from the small size of the oil globules, wherein said small size can be obtained for example by using a high-pressure homogenizer. Nanoemulsions are to be distinguished from microemulsions by their structure. Microemulsions are thermodynamically stable dispersions comprising micelles of at least one amphiphilic lipid swollen with oil. Furthermore, microemulsions do not require considerable mechanical energy to be prepared. They form spontaneously simply by placing the constituents in contact. At least one possible drawback of microemulsions can be associated with the presence of a high proportion of surfactants, which may tend to lead to intolerance and entailing a sticky feel when applied to the skin. Moreover, their field of formulation is generally narrow and their temperature stability can be limited.

The at least one (as used throughout herein above and below, the expression "at least one" means one or more and thus includes individual components as well as mixtures/combinations) amphiphilic lipid is present in an amphiphilic lipid phase, which comprises at least one amphiphilic lipid chosen from for example nonionic and ionic amphiphilic lipids. The expression "amphiphilic lipid" means any molecule of bipolar structure comprising at least one hydrophobic portion and at least one hydrophilic portion having the property of reducing the surface tension of water (g<55 mN/m) and of reducing the interface tension between water and an oily phase. The synonyms of amphiphilic lipid are, for example: surfactant, surface agent, and emulsifier.

The prior art discloses nanoemulsions comprising an amphiphilic lipid phase comprising phospholipids, a cationic lipid, water and a hydrophobic sunscreen. They are obtained by a high-pressure homogenization process. These nanoemulsions can have at least one drawback, for example, such nanoemulsions may tend to be unstable on storage at the conventional storage temperatures, i.e., between 0° C. and 45° C. Such nanoemulsions may lead to yellow compositions and may produce unpleasant odors, which may develop after a few days of storage. Furthermore, such nanoemulsions tend to exhibit less favorable cosmetic properties. They are described in the "DCI" review of April 1996, pages 46-48, the disclosure of which is incorporated by reference herein.

Moreover, documents EP-A-728 460 and EP-A-780 114, the disclosures of which are incorporated by reference herein, disclose nanoemulsions based on fluid nonionic amphiphilic lipids and on silicone surfactants.

However, all these nanoemulsions are fluid. For certain uses, products are sought which can be measured out and taken up easily by hand. To do this, these products must have a certain level of consistency or viscosity. Specifically, a liquid product may be more difficult to measure out and tends to run easily between the fingers.

It is known practice to use, as thickeners for aqueous media, water-soluble or water-dispersible polymers, such as optionally crosslinked polymers for example polycarboxyvinylic acids, such as carbopol, wherein said polymers can have a long chain length and a high molecular weight.

When such polymers are used in compositions in the form of nanoemulsions, some of such nanoemulsions may tend to exhibit a decrease in at least one characteristic, such as stability and transparency.

Thus, there is still a need for a thickening system which can conveniently thicken, or even gel, a composition in the form of an oil-in-water nanoemulsion, while minimizing any possible influence that it may have on the cosmetic properties of said compositions.

The inventors have discovered, unexpectedly, that oil-in-water nanoemulsions comprising oil globules with an average size of less than 150 nm comprising at least one oil and at least one amphiphilc lipid can be thickened with at least one non-ionic polymer, for example at least one non-ionic polymer chosen from water-soluble and water-dispersible non-ionic polymers comprising at least one hydrophobic block and at least one hydrophilic block.

One subject of the present invention is oil-in-water nanoemulsions comprising oil globules with an average size of less than 150 nm comprising at least one oil, at least one amphiphilc lipid, and at least one nonionic polymer comprising at least one hydrophobic block and at least one hydrophilic block, wherein the weight ratio of the amount of said at least one oil to the amount of said at least one amphiphilic lipid ranges for example from 1:1 to 10:1, such as for example from 1.2:1 to 6:1.

Another subject of the invention is a process for thickening oil-in-water nanoemulsions comprising oil globules with an average size of less than 150 nm comprising at least one oil and at least one amphiphilc lipid comprising including at least one nonionic polymer comprising at least one hydrophobic block and at least one hydrophilic block in said nanoemulsions.

As a non-restrictive explanation, it may be considered that, in the context of the invention, the increase in the viscosity of the medium may result from the formation of a network of oil particles, said network involving combinations of hydrophobic type between, on the one hand, the hydrophobic groups of the polymer and, on the other hand, the hydrophobic cores of the oil particles. The existence of labile bonds between the particles may be responsible in part for increasing the viscosity of the mixture.

The nanoemulsions in accordance with the invention are prepared at temperatures ranging for example from 4° C. to 45° C. and are compatible with heat-sensitive active agents. If desired, the nanoemulsions can comprise large amounts of oil. Such nanoemulsions can for example comprise large amounts of fragrance and can improve their remanence. They can also promote the penetration of the active agents into the superficial layers of the skin and the deposition of active agent onto keratin fibres such as the hair. Hair treated with these nanoemulsions may be at least one of the following: shiny, while simultaneously avoiding a greasy look or feel, softer and more lively in nature, while also tending to disentangle easily.

The cosmetic composition, such as for example a hair composition, obtained by comprising the nanoemulsions of the present invention may spread easily, may be easier to handle and may be removed satisfactorily by rinsing.

The at least one nonionic polymer, which is for example chosen from water-soluble and water-dispersible nonionic polymers, comprises at least one hydrophobic block and at least one hydrophilic block. The at least one nonionic polymer can for example comprise at least two hydrophobic blocks.

The at least one hydrophobic block can be chosen from fatty chains comprising from 6 to 30 carbon atoms, such as for example hydrocarbon-based chains chosen from alkyl, aryl ($C_1$-$C_8$)alkyl, ($C_1$-$C_8$)alkylaryl and alkenyl chains, divalent aliphatic groups such as for example $C_4$-$C_{30}$ alkylene, divalent cycloaliphatic groups such as, for example, methylene dicyclohexyl and isophorone, and divalent aromatic groups such as phenylene. The aryl groups can be chosen from phenyl, naphthyl and anthryl groups.

The at least one hydrophilic block may be chosen from, for example, polyethylene oxides, polysaccharides, polyamides, such as polyacrylamide, and polyesters. In one embodiment of the invention, the at least one hydrophilic block may be chosen from polyethylene oxides comprising from 15 to 500 ethylene oxides.

In general, the at least one hydrophobic block and the at least one hydrophilic block for example can be bonded by way of at least one linking group chosen from, for example, ester, ether, urea, amide and urethane linkers.

The weight ratio of the at least one hydrophilic block to the at least one hydrophobic block of the polymer generally ranges for example from 10:1 to 1000:1.

The at least one nonionic polymer according to the invention (uncharged "hydrophobic" polymer) can be chosen from:
(1) celluloses modified with at least one group comprising at least one hydrophobic chain such as, for example:
    hydroxyethylcelluloses modified by at least one group comprising at least one fatty chain such as alkyl, arylalkyl, alkylaryl, and alkenyl groups and further such as alkyl, arylalkyl, alkylaryl, and alkenyl groups wherein said alkyl groups and said alkenyl groups comprise from 8 to 22 carbon atoms, such as the product NATROSOL PLUS GRADE 330 CS($C_{16}$ alkyls) sold by the company AQUALON, and the product BERMOCOLL EHM 100 sold by the company BEROL NOBEL, and
    hydroxyethylcelluloses modified by at least one polyalkylene glycol ($C_6$-$C_{20}$)alkylphenyl ether group, such as the product AMERCELL POLYMER HM-1500 (polyethylene glycol (15) ether of nonylphenol) sold by the company AMERCHOL;
(2) hydroxypropylguars modified by at least one group comprising at least one $C_{10}$-$C_{30}$ fatty chain such as the product ESAFLOR HM 22 ($C_{22}$ alkyl chain) sold by the company LAMBERTI, the products Miracare XC95-3 ($C_{14}$ alkyl chain) and RE 205-1 ($C_{20}$ alkyl chain) sold by the company Rhodia Chimie; and
(3) polyether-polyurethanes comprising in their chain at least one hydrophilic block which is most often of a polyoxyethylenated nature and at least one hydrophobic block which may be a chain chosen from aliphatic chains, cycloaliphatic chains, and aromatic chains.

The polyether-polyurethanes can, for example, comprise at least two lipophilic (i.e., hydrophobic) hydrocarbon chains comprising from 6 to 30 carbon atoms, separated by a hydrophilic block, it being possible for the hydrocarbon chains to be chosen from pendant chains and chains at the end of a hydrophilic block. One embodiment may comprise at least one pendant chain. In addition, the polymer may comprise a hydrocarbon chain at at least one end of a hydrophilic block.

Representative polyether-polyurethanes useful in the present invention may be multiblocks, such as in triblock form. The hydrophobic blocks may be at each end of the chain (for example: triblock copolymer with hydrophilic central block) and optionally both at the ends and in the chain (multiblock copolymer for example). These same polymers may also be in the form of graft units or may be star-shaped.

The nonionic polyether-polyurethanes may be triblock copolymers whose hydrophilic block is a polyoxyethylenated chain comprising from 50 to 1000 oxyethylenated groups. Certain nonionic polyether-polyurethanes comprise a urethane bond between the hydrophilic blocks.

By extension, polyether-polyurethanes whose hydrophilic blocks are linked by other chemical bonds to the lipophilic blocks are also included among the nonionic polyether-polyurethanes.

Representative nonionic polyether-polyurethanes can include, for example, polyether-polyurethanes comprising at least one polyoxyethylenated chain and at least one fatty chain, chosen from, for example, $C_8$-$C_{30}$ alkyl and alkenyl groups. For instance, such polyether-polyurethanes can include the products Dapral T 210 and Dapral T 212 sold by the company Akzo, and the products Aculyn 44 and Aculyn 46 from the company ROHM and HMS [ACULYN 46 is a polycondensate of polyethylene glycol comprising 150 or 180 mol of ethylene oxide, stearyl alcohol and methylenebis (4-cyclohexylisocyanate) (SMDI), at 15% by weight in a maltodextrin (4%) and water (81%) matrix; ACULYN 44 is a polycondensate of polyethylene glycol comprising 150 or 180 mol of ethylene oxide, decyl alcohol and methylenebis (4-cyclohexylisocyanate) (SMDI), at 35% by weight in a propylene glycol (39%) and water (26%) mixture].

As examples of nonionic polyether-polyurethanes that can be used in the invention, mention may also be made of the polymer SER-AD FX1100 sold by the company Servo Delden, which comprises an oxyethylene unit and two $C_{18}$ hydrocarbon-based groups at the end of the chain linked to the ethylene oxide via a polyurethane block.

Representative nonionic polyether-polyurethanes include Rhéolate 205 comprising a urea function sold by the company RHEOX and Rhéolate 208, 204 and 212, as well as Acrysol RM 184 from the company Rohm & Haas.

There may also be mentioned the product ELFACOS T210 comprising a $C_{12}$-$C_{14}$ alkyl chain and the product ELFACOS T212 comprising a $C_{18}$ alkyl chain from AKZO.

The product DW 1206B from RHOM & HAAS comprising a $C_{20}$ alkyl chain and with a urethane bond, sold at 20% dry matter content in water, may also be used.

It is also possible to use solutions and dispersions of these polymers for example in water and for example in an aqueous-alcoholic medium. By way of example of such polymers, there may be mentioned SER-AD FX1010 and SER-AD 1035 sold by the company Hüls, Rhéolate 255, Rhéolate 278 and Rhéolate 244 sold by the company RHEOX. It is also possible to use the products DW 1206F and DW 1206J provided by the company ROHM & HAAS.

Representative polyether-polyurethanes that can be used according to the invention include polyether-polyurethanes described in the article by G. Formum, J. Bakke and Fk.

Hansen—Colloid Polym. Sci 271, 380-389 (1993), the disclosure of which is incorporated by reference herein.

Additionally, the at least one nonionic polymer according to the invention can be chosen from:

(4) copolymers formed from vinylpyrrolidone and at least one hydrophobic monomer comprising at least one fatty chain such as for example:
- the products ANTARON V216 and GANEX V216 (vinylpyrrolidone/hexadecene copolymer) sold by the company I.S.P., and
- the products ANTARON V220 and GANEX V220 (vinylpyrrolidone/eicosene copolymer) sold by the company I.S.P.;

(5) copolymers formed from at least one $C_1$-$C_6$ alkyl methacrylate and at least one amphiphilic monomer comprising at least one fatty chain and copolymers formed from at least one $C_1$-$C_6$ alkyl acrylate and at least one amphiphilic monomer comprising at least one fatty chain such as for example the oxyethylenated stearyl acrylate/methyl acrylate copolymer sold by the company GOLDSCHMIDT under the name ANTIL 208; and (6) copolymers formed from at least one hydrophilic methacrylate and at least one hydrophobic monomer comprising at least one fatty chain and copolymers formed from at least one hydrophilic acrylate and at least one hydrophobic monomer comprising at least one fatty chain, such as, for example, the polyethylene glycol methacrylate/lauryl methacrylate copolymer;

In the compositions according to the invention, the at least one nonionic polymer comprising at least one hydrophobic block and at least one hydrophilic block is generally present in an amount ranging for example from 0.01% to 10% by weight relative to the total weight of the composition, such as from 0.1% to 5% by weight relative to the total weight of the composition.

The nanoemulsions according to the present invention can comprise at least one amphiphilic lipid chosen from for example nonionic amphiphilic lipids and anionic amphiphilic lipids.

The nonionic amphiphilic lipids of the invention can be chosen from, for example:

1/—silicone surfactants,

2/—nonionic amphiphilic lipids that are fluid at a temperature of less than or equal to 45° C. chosen from esters formed from (i) at least one polyol chosen from polyethylene glycol comprising from 1 to 60 ethylene oxide units, sorbitan, glycerol comprising from 2 to 30 ethylene oxide units, and polyglycerols comprising from 2 to 15 glycerol units, and (ii) at least one fatty acid comprising at least one alkyl chain chosen from saturated and unsaturated, linear and branched $C_8$-$C_{22}$ alkyl chains, 3/—mixed esters derived from (i) at least one fatty acid, at least one carboxylic acid, and glycerol, and mixed esters derived from (ii) at least one fatty alcohol, at least one carboxylic acid, and glycerol, wherein said at least one carboxylic acid is chosen from α-hydroxy acids and succinic acid, 4/—fatty acid esters of sugars and fatty alcohol ethers of sugars, 5/—surfactants that are solid at a temperature of less than or equal to 45° C. chosen from fatty esters of glycerol, fatty esters of sorbitan, oxyethylenated fatty esters of sorbitan, ethoxylated fatty ethers, and ethoxylated fatty esters, and 6/—block copolymers of ethylene oxide (A) and of propylene oxide (B).

1/ The silicone surfactants that can be used according to the invention are silicone compounds comprising at least one oxyalkylene chain chosen from oxyethylene —$OCH_2CH_2$— and oxypropylene —$OCH_2CH_2CH_2$—. Representative silicone surfactants that can be used according to the present invention include silicone surfactants disclosed in U.S. Pat. Nos. 5,364,633 and 5,411,744, the disclosures of which are incorporated by reference herein.

The silicone surfactants used according to the present invention can be chosen for example from compounds of formula (I):

$$R_1-\underset{\underset{CH_3}{|}}{\overset{\overset{CH_3}{|}}{Si}}-O+\underset{\underset{CH_3}{|}}{\overset{\overset{CH_3}{|}}{Si}}-O\Big]_A+\underset{\underset{R_2}{|}}{\overset{\overset{CH_3}{|}}{Si}}-O\Big]_B+\underset{\underset{CH_3}{|}}{\overset{\overset{CH_3}{|}}{Si}}-R_3 \quad (I)$$

in which:

$R_1$, $R_2$ and $R_3$, which may be identical or different, are each chosen from $C_1$-$C_6$ alkyl groups and groups of the formula —$(CH_2)_x$—$(OCH_2CH_2)_y$—$(OCH_2CH_2CH_2)_z$—$OR_4$, provided that at least one of said groups $R_1$, $R_2$ and $R_3$ is not a $C_1$-$C_6$ alkyl group;

$R_4$ is chosen from hydrogen, alkyl groups, and acyl groups;

A is chosen from integers ranging from 0 to 200;

B is chosen from integers ranging from 0 to 50; with the proviso that A and B are not simultaneously equal to zero;

x is chosen from integers ranging from 1 to 6;

y is chosen from integers ranging from 1 to 30;

z is chosen from integers ranging from 0 to 5.

In one embodiment of the invention, in the compound of formula (I) said alkyl groups are methyl groups, x is chosen from integers ranging from 2 to 6 and y is chosen from integers ranging from 4 to 30.

Representative examples of silicone surfactants of formula (I) can include the compounds of formula (II):

$$(H_3C)_3Si-O+\begin{bmatrix}\overset{CH_3}{\underset{CH_3}{|}}\\Si-O\end{bmatrix}_A+\begin{bmatrix}\overset{CH_3}{|}\\Si-O\\\underset{(CH_2)_2(OCH_2CH_2)_yOH}{|}\end{bmatrix}_B Si(CH_3)_3 \quad (II)$$

in which A is chosen from integers ranging from 20 to 105, B is chosen from integers ranging from 2 to 10 and y is chosen from integers ranging from 10 to 20.

Representative examples of silicone surfactants of formula (I) can include the compounds of formula (III):

$$H-(OCH_2CH_2)_y-(CH_2)_3-[(CH_3)_2SiO]_{A'}-(CH_2)_3-(OCH_2CH_2)_y-OH \quad (III)$$

in which A' and y, which may be identical or different, are each chosen from integers ranging from 10 to 20.

Silicone surfactants of the invention which may be used for example are the silicone surfactants sold by the company Dow Corning under the names DC 5329, DC 7439-146, DC 2-5695, and Q4-3667. The products DC 5329, DC 7439-146, and DC 2-5695 are silicone surfactants of formula (II) in which, respectively, A is 22, B is 2, and y is 12; A is 103, B is 10, and y is 12; A is 27, B is 3, and y is 12.

The product Q4-3667 is a compound of formula (III) in which A is 15 and y is 13.

2/ The amphiphilic lipids that are fluid at a temperature of less than or equal to 45° C. are chosen from, for example:
- the isostearate of polyethylene glycol of molecular weight 400, sold under the name PEG 400 by the company Unichema;
- diglyceryl isostearate, sold by the company Solvay;
- glyceryl laurate comprising 2 glycerol units, sold by the company Solvay;
- sorbitan oleate, sold under the name SPAN 80 by the company ICI;
- sorbitan isostearate, sold under the name NIKKOL SI 10R by the company Nikko;
- α-butylglucoside cocoate and α-butylglucoside caprate, sold by the company Ulice.

3/ The mixed esters derived from (i) at least one fatty acid, at least one carboxylic acid, and glycerol, and the mixed esters derived from (ii) at least one fatty alcohol, at least one carboxylic acid, and glycerol, wherein said at least one carboxylic acid is chosen from α-hydroxy acids and succinic acid, which can be used as surfactants in the nanoemulsion according to the invention, may be chosen from, for example, (a) mixed esters derived from at least one fatty acid comprising at least one alkyl chain comprising from 8 to 22 carbon atoms, at least one α-hydroxy acid, and glycerol, (b) mixed esters derived from at least one fatty acid comprising at least one alkyl chain comprising from 8 to 22 carbon atoms, succinic acid, and glycerol, (c) mixed esters derived from at least one fatty alcohol comprising at least one alkyl chain comprising from 8 to 22 carbon atoms, at least one α-hydroxy acid, and glycerol, and (d) mixed esters derived from at least one fatty alcohol comprising at least one alkyl chain comprising from 8 to 22 carbon atoms, succinic acid, and glycerol. The α-hydroxy acid may be chosen, for example, from at least one acid chosen from citric acid, lactic acid, glycolic acid and malic acid.

The alkyl chain of the fatty acids and fatty alcohols from which are derived the mixed esters which can be used in the nanoemulsion of the invention may be chosen from linear and branched, saturated and unsaturated alkyl chains. For example, the alkyl chain may be at least one chain chosen from stearate, isostearate, linoleate, oleate, behenate, arachidonate, palmitate, myristate, laurate, caprate, isostearyl, stearyl, linoleyl, oleyl, behenyl, myristyl, lauryl and capryl chains.

As examples of mixed esters which can be used in the nanoemulsion of the invention, mention may be made of the mixed ester of glycerol and of the mixture of citric acid, lactic acid, linoleic acid and oleic acid (CTFA name: Glyceryl citrate/lactate/linoleate/oleate) sold by the company Hüls under the name Imwitor 375; the mixed ester of succinic acid and of isostearyl alcohol with glycerol (CTFA name: Isostearyl diglyceryl succinate) sold by the company Hüls under the name Imwitor 780 K; the mixed ester of citric acid and of stearic acid with glycerol (CTFA name: Glyceryl stearate citrate) sold by the company Hüls under the name Imwitor 370; the mixed ester of lactic acid and of stearic acid with glycerol (CTFA name: Glyceryl stearate lactate) sold by the company Danisco under the name Lactodan B30 or Rylo LA30.

4/ Fatty acid esters of sugars, which can be used as surfactants in the nanoemulsion according to the invention, can be chosen from fatty acid esters of sugars that are solid at a temperature of less than or equal to 45° C., such as esters derived from at least one $C_8$-$C_{22}$ fatty acid and at least one sugar chosen from sucrose, maltose, glucose, and fructose, and esters derived from at least one $C_{14}$-$C_{22}$ fatty acid and methylglucose.

The $C_8$-$C_{22}$ and $C_{14}$-$C_{22}$ fatty acids forming the fatty unit of the esters which can be used in the nanoemulsion of the invention comprise an alkyl chain chosen from saturated and unsaturated linear alkyl chains comprising, respectively, from 8 to 22 and from 14 to 22 carbon atoms. The fatty unit of the esters may be formed for example from stearates, behenates, arachidonates, palmitates, myristates, laurates and caprates. In one embodiment of the invention, stearates for example may be used as the fatty unit.

As examples of esters of at least one fatty acid and of sucrose, of fatty acids and of maltose, of fatty acids and of glucose, and of fatty acids and of fructose, mention may be made of sucrose monostearate, sucrose distearate and sucrose tristearate and mixtures thereof, such as the products sold by the company Croda under the name Crodesta F50, F70, F110 and F160 having, respectively, an HLB (hydrophilic lipophilic balance) of 5, 7, 11 and 16; and examples of esters of at least one fatty acids and of methylglucose which may be mentioned are methylglucose polyglyceryl-3 distearate, sold by the company Goldschmidt under the name Tego-care 450. Mention may also be made of glucose or maltose monoesters such as methyl o-hexadecanoyl-6-D-glucoside and o-hexadecanoyl-6-D-maltoside.

The fatty alcohol ethers of sugars, which can be used as surfactants in the nanoemulsion according to the invention, are solid at a temperature of less than or equal to 45° C. and may be chosen for example from ethers of at least one $C_8$-$C_{22}$ fatty alcohol and of glucose, of at least one $C_8$-$C_{22}$ fatty alcohol and of maltose, of at least one $C_8$-$C_{22}$ fatty alcohol and of sucrose, and of at least one $C_8$-$C_{22}$ fatty alcohol and of fructose, and ethers of at least one $C_{14}$-$C_{22}$ fatty alcohol and of methylglucose. An example of such an ether would include, among other ethers, alkylpolyglucosides.

The at least one $C_8$-$C_{22}$ and the at least one $C_{14}$-$C_{22}$ fatty alcohols forming the fatty unit of the ethers which may be used in the nanoemulsion of the invention can comprise at least one alkyl chain chosen from saturated and unsaturated, linear alkyl chains comprising, respectively, from 8 to 22 and from 14 to 22 carbon atoms. The fatty unit of the ethers may be chosen for example from decyl, cetyl, behenyl, arachidyl, stearyl, palmityl, myristyl, lauryl, capryl and hexadecanoyl units, and further such as cetearyl.

As examples of fatty alcohol ethers of sugars, mention may be made of alkylpolyglucosides such as decylglucoside and laurylglucoside, which is sold, for example, by the company Henkel under the respective names Plantaren 2000 and Plantaren 1200, cetostearyl glucoside optionally as a mixture with cetostearyl alcohol, sold for example, under the name Montanov 68 by the company SEPPIC, under the name Tego-care CG90 by the company Goldschmidt and under the name Emulgade KE3302 by the company Henkel, as well as arachidyl glucoside, for example in the form of a mixture of arachidyl alcohol and behenyl alcohol and arachidyl glucoside, sold under the name Montanov 202 by the company SEPPIC.

In one embodiment of the invention, the surfactant used can be for example at least one surfactant chosen from sucrose monostearate, sucrose distearate and sucrose tristearate. Additional surfactants that can be used include methylglucose polyglyceryl-3 distearate and alkylpolyglucosides.

5/ The fatty esters of glycerol which may be used as surfactants in the nanoemulsion according to the invention, which are solid at a temperature of less than or equal to 45° C., may be chosen for example from esters formed from at least one acid comprising a saturated linear alkyl chain comprising from 16 to 22 carbon atoms and from 1 to 10 glycerol units. One or more of these fatty esters of glycerol may be used in the nanoemulsion of the invention.

These esters may be chosen for example from stearates, behenates, arachidates and palmitates. In one embodiment, the esters may be chosen for example from stearates and palmitates.

As examples of surfactants which can be used in the nanoemulsion of the invention, mention may be made of decaglyceryl monostearate, distearate, tristearate and pentastearate (CTFA names: Polyglyceryl-10 stearate, Polyglyceryl-10 distearate, Poly-glyceryl-10 tristearate, Polyglyceryl-10 pentastearate), such as the products sold under the respective names Nikkol Decaglyn 1-S, 2-S, 3-S and 5-S by the company Nikko, and diglyceryl monostearate (CTFA name: Polyglyceryl-2 stearate), such as the product sold by the company Nikko under the name Nikkol DGMS.

The fatty esters of sorbitan which may be used as surfactants in the nanoemulsion according to the invention are solid at a temperature of less than or equal to 45° C. and are chosen from $C_{16}$-$C_{22}$ fatty acid esters of sorbitan and oxyethylenated $C_{16}$-$C_{22}$ fatty acid esters of sorbitan. They are formed from (i) at least one fatty acid comprising at least one saturated linear alkyl chain comprising, respectively, from 16 to 22 carbon atoms, and from sorbitol, as well as from (ii) at least one fatty acid comprising at least one saturated linear alkyl chain comprising, respectively, from 16 to 22 carbon atoms, and from ethoxylated sorbitol. The oxyethylenated esters generally comprise from 1 to 100 ethylene glycol units, such as from 2 to 40 ethylene oxide (EO) units.

These esters may be chosen for example from stearates, behenates, and arachidates, palmitates. In one embodiment, the esters may be chosen for example from stearates and palmitates.

As examples of surfactants which can be used in the nanoemulsion of the invention, mention may be made of sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: Polysorbate 65), sold by the company ICI under the name Tween 65.

The ethoxylated fatty ethers that are solid at a temperature of less than or equal to 45° C., which may be used as surfactants in the nanoemulsion according to the invention, can be ethers formed from 1 to 100 ethylene oxide units and from at least one fatty alcohol chain comprising from 16 to 22 carbon atoms. The at least one fatty chain of the ethers may be chosen for example from behenyl, arachidyl, stearyl and cetyl units, and further for example from cetearyl. Examples of ethoxylated fatty ethers which may be mentioned are behenyl alcohol ethers comprising 5, 10, 20 and 30 ethylene oxide units (CTFA names: Beheneth-5, Beheneth-10, Beheneth-20, Beheneth-30), such as the products sold under the names Nikkol BB5, BB10, BB20 and BB30 by the company Nikko, and stearyl alcohol ether comprising 2 ethylene oxide units (CTFA name: steareth-2), such as the product sold under the name Brij 72 by the company ICI.

The ethoxylated fatty esters that are solid at a temperature of less than or equal to 45° C., which may be used as surfactants in the nanoemulsion according to the invention, are esters formed from 1 to 100 ethylene oxide units and from at least one fatty acid chain comprising from 16 to 22 carbon atoms. The at least one fatty chain in the esters may be chosen for example from stearate, behenate, arachidate and palmitate units. Examples of ethoxylated fatty esters which may be mentioned are the ester of stearic acid comprising 40 ethylene oxide units, such as the product sold under the name Myrj 52 (CTFA name: PEG-40 stearate) by the company ICI, as well as the ester of behenic acid comprising 8 ethylene oxide units (CTFA name: PEG-8 behenate), such as the product sold under the name Compritol HD5 ATO by the company Gattefosse.

6/ The block copolymers of ethylene oxide (A) and of propylene oxide (B), which may be used as a surfactant in the nanoemulsion according to the invention, may be chosen for example from at least one block copolymer of formula (I):

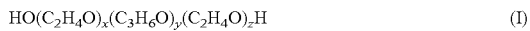

$$HO(C_2H_4O)_x(C_3H_6O)_y(C_2H_4O)_zH \qquad (I)$$

in which x, y, and z, which may be identical or different, are each chosen from integers wherein x+z is an integer ranging from 2 to 100 and y is an integer ranging from 14 to 60, and optionally having an HLB value ranging from 2 to 16.

The at least one block copolymer of formula (I) may be chosen for example from poloxamers, such as Poloxamer 231, and further such as the product sold by the company ICI under the name PLURONIC L81, which corresponds to the block copolymer of formula (I) wherein x=z=6, y=39 (HLB 2); Poloxamer 282, such as the product sold by the company ICI under the name PLURONIC L92, which corresponds to the block copolymer of formula (I) wherein x=z=10, y=47 (HLB 6); and Poloxamer 124, such as the product sold by the company ICI under the name PLURONIC L44, which corresponds to the block copolymer of formula (I) wherein x=z=11, y=21 (HLB 16).

Representative nonionic amphiphilic lipids that can be used for example are chosen from:
  polyethylene glycol isostearate (8 mol of ethylene oxide),
  diglyceryl isostearate,
  polyglyceryl monolaurate, polyglyceryl monostearate, and polyglyceryl distearate which comprise 10 glycerol units,
  sorbitan oleate, and
  sorbitan isostearate.

Representative anionic amphiphilic lipids of the invention, for example, can be chosen from:
  alkyl ether citrates,
  alkoxylated alkenyl succinates,
  alkoxylated glucose alkenyl succinates, and
  alkoxylated methylglucose alkenyl succinates.

The alkyl ether citrates which may be used as surfactants in the nanoemulsion according to the invention may be chosen for example from at least one alkyl ether citrate chosen from monoesters, diesters, and triesters formed from citric acid and from at least one oxyethylenated fatty alcohol comprising at least one alkyl chain chosen from linear and branched, saturated and unsaturated alkyl chains comprising from 8 to 22 carbon atoms, and comprising from 3 to 9 ethoxylated groups. One embodiment of the invention may comprise at least one of the above-mentioned citrates in the nanoemulsion. Another embodiment may comprise at least two of the above-mentioned citrates in the nanoemulsion.

These citrates may be chosen, for example, from the monoesters, diesters, and triesters of citric acid and of ethoxylated lauryl alcohol, comprising from 3 to 9 ethoxylated groups, which are, for example, sold by the company Witco under the name WITCONOL EC. For example, WITCONOL EC 2129, which is predominantly a dilaureth-9 citrate, and Witconol EC 3129, which is predominantly a trilaureth-9 citrate, can be chosen.

When used, the alkyl ether citrates used as surfactants can for example be neutralized to a pH of about 7 with at least one base chosen from inorganic bases (such as sodium hydroxide, potassium hydroxide and ammonia) and organic bases (such as mono-ethanolamine, diethanolamine, triethanolamine, 1,3-aminomethylpropanediol, N-methylglucamine and basic amino acids like arginine and lysine).

The alkenyl succinates which may be used as surfactants in the nanoemulsion of the invention can, for example, be chosen from alkoxylated alkenyl succinates, alkoxylated glucose alkenyl succinates, and alkoxylated methylglucose alkenyl succinates that correspond to compounds of formulae (I) and (II):

$$HOOC\text{—}CHR\text{—}CH_2\text{—}COO\text{-}E \quad (I)$$

$$HOOC\text{—}CHR\text{—}CH_2\text{—}COO\text{-}E\text{-}O\text{—}CO\text{—}CH_2\text{—}CHR'\text{—}COOH \quad (II)$$

in which:
- R and R', which may be identical or different, are each chosen from linear and branched alkenyl groups comprising from 6 to 22 carbon atoms,
- E is chosen from oxyethylene chains of formula $(C_2H_4O)_n$ in which n is chosen from integers ranging from 2 to 100, oxypropylene chains of formula $(C_3H_6O)_{n'}$ in which n' is chosen from integers ranging from 2 to 100, and random and block copolymers comprising chains chosen from oxyethylene chains of formula $(C_2H_4O)_n$ and oxypropylene chains of formula $(C_3H_6O)_{n'}$ (such as oxyethylenated glucose copolymers, oxyethylenated methylglucose copolymers, oxypropylenated glucose copolymers, and oxypropylenated methylglucose copolymers) such that:
    the sum of n and n' is an integer ranging from 2 to 100,
    the oxyethylenated and oxypropylenated glucose groups of said oxyethylenated and oxypropylenated glucose copolymers comprise on average from 4 to 100, respectively, oxyethylene or oxypropylene units distributed on all the hydroxyl functions, and
    the oxyethylenated and oxypropylenated methylglucose groups of said oxyethylenated and oxypropylenated methyl glucose copolymers comprise on average from 4 to 100 oxyethylene or oxypropylene units distributed on all the hydroxyl functions.

In formulae (I) and (II), n and n' are average values and are thus not necessarily integers. In one embodiment of the invention, n is chosen from integers ranging from 5 to 60, such as from 10 to 30.

In one embodiment, R and R', which may be identical or different, are each chosen from linear alkenyl groups comprising from 8 to 22 carbon atoms, such as from 14 to 22 carbon atoms. R and R', which may be identical or different, each may be, for example, chosen from the hexadecenyl group comprising 16 carbon atoms and the octadecenyl group comprising 18 carbon atoms.

The compounds of formulae (I) and (II) described above, in which E is chosen from oxyethylene chains, oxypropylene chains and copolymers comprising oxyethylene chains and oxypropylene chains, may be prepared in accordance with the description given in documents WO-A-94/00508, EP-A-107 199 and GB-A-2 131 820, which are incorporated herein by reference.

The acid function —COOH in the surfactants of formulae (I) and (II) is generally in the nanoemulsion of the invention in a form which is neutralized with a neutralizing agent chosen, for example, from inorganic bases (such as sodium hydroxide, potassium hydroxide and ammonia) and organic bases (such as monoethanolamine, diethanolamine, triethanolamine, 1,3-aminomethylpropanediol, N-methylglucamine, and basic amino acids, such as arginine and lysine).

Representative surfactants which can be used in the nanoemulsion of the invention, include at least one surfactant chosen from hexadecenyl succinate 18 EO (compound of formula (I) with R=hexadecenyl, $E=(C_2H_4O)_n$, n=18), hexadecenyl succinate 45 EO (compound of formula (I) with R=hexadecenyl, $E=(C_2H_4O)_n$, n=45), dihexadecenyl succinate 18 EO (compound of formula (II) with R=R'=hexadecenyl, $E=(C_2H_4O)_n$, n=18), dihexadecenyl glucose succinate 10 EO (compound of formula (II) with R=R'=hexadecenyl, E=oxyethylenated glucose containing 10 oxyethylene groups), dihexadecenyl glucose succinate 20 EO (compound of formula (II) with R=R'=hexadecenyl, E=oxyethylenated glucose containing 20 oxyethylene groups), and dioctadecenyl methylglucose succinate 20 EO (compound of formula (II) with R=R'=octadecenyl, E=oxyethylenated methylglucose containing 20 oxyethylene groups).

The at least one amphiphilic lipid chosen from nonionic amphiphilic lipids and anionic amphiphilic lipids may be present in the aqueous phase (if more hydrophilic in nature) or in the oily phase (if more lipophilic in nature) of the nanoemulsion.

The at least one amphiphilic lipid chosen from nonionic amphiphilic lipids and anionic amphiphilic lipids may be present in the nanoemulsion of the invention in an amount ranging, for example, from 0.2% to 15% by weight relative to the total weight of the nanoemulsion, such as from 1% to 8% by weight relative to the total weight of the nanoemulsion.

The weight ratio of the amount of oily phase with respect to the amount of the at least one amphiphilic lipid (surfactant) ranges for example from 1:1 to 10:1, such as from 1.2:1 to 10:1, further such as from 1.5:1 to 6:1, and furthermore such as from 2:1 to 5:1. The expression "amount of oily phase" herein means the total amount of constituents of this phase excluding the amount of the at least one amphiphilic lipid chosen from nonionic amphiphilic lipids and anionic amphiphilic lipids.

In one embodiment of the invention, the nanoemulsion of the invention may also comprise at least one additional ionic amphiphilic lipid other than the ionic amphiphilic lipids described above. Such additional ionic amphiphilic lipids may be added to possibly further improve the stability of the dispersion.

The at least one additional ionic amphiphilic lipid which may be used in the nanoemulsions of the invention can, for example, be chosen from cationic amphiphilic lipids and anionic amphiphilic lipids other than the anionic amphiphilic lipids described above, such as from:
- alkaline salts of dicetyl phosphate and of dimyristyl phosphate;
- alkaline salts of cholesteryl sulfate;
- alkaline salts of cholesteryl phosphate;
- lipoamino acids and salts thereof, such as monosodium and disodium acylglutamates, for instance the disodium salt of N-stearoyl-L-glutamic acid, sold under the name ACYLGLUTAMATE HS21 by Ajinomoto;
- sodium salts of phosphatidic acid;
- phospholipids; and
- alkylsulfonic derivatives of formula:

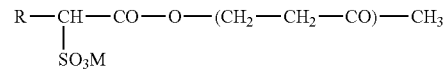

in which R, which may be identical or different in embodiments wherein more than one of said alkylsulfonic derivative is used, is chosen from $C_{16}$-$C_{22}$ alkyl groups, such as $C_{16}H_{33}$ and $C_{18}H_{37}$ groups, and M is chosen from alkali metals and alkaline-earth metals, such as sodium.

Representative cationic amphiphilic lipids that can be used in the nanoemulsions of the invention can be chosen from, for example, quaternary ammonium salts, fatty amines, and salts thereof.

The quaternary ammonium salts are, for example, chosen from:

A) quaternary ammonium salts of formula (IV) below:

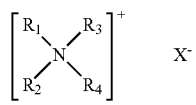

(IV)

in which:

R₁, R₂, R₃, and R₄, which may be identical or different, are each chosen from linear and branched aliphatic groups comprising from 1 to 30 carbon atoms, and aromatic groups, such as aryl and alkylaryl groups. The aliphatic groups can comprise hetero atoms, such as oxygen, nitrogen, and sulfur, and halogens. And the aliphatic groups can be chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate, and hydroxyalkyl groups comprising from 1 to 30 carbon atoms;

$X^-$ is an anion chosen from halides, phosphates, acetates, lactates, ($C_2$-$C_6$)alkyl sulfates, alkyl sulfonates, and alkylaryl sulfonates;

B) quaternary ammonium salts of imidazolinium, such as, for example, the salts of formula (V) below:

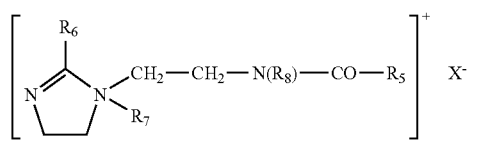

(V)

in which:

R₅ is chosen from alkenyl and alkyl groups comprising from 8 to 30 carbon atoms, for example groups derived from tallow fatty acid, R₆ is chosen from a hydrogen atom, $C_1$-$C_4$ alkyl groups, and alkenyl and alkyl groups comprising from 8 to 30 carbon atoms, R₇ is chosen from $C_1$-$C_4$ alkyl groups, R₈ is chosen from a hydrogen atom and $C_1$-$C_4$ alkyl groups, $X^-$ is an anion chosen from halides, phosphates, acetates, lactates, alkyl sulfates, alkyl sulfonates, and alkylaryl sulfonates.

In one embodiment, for example, R₅ and R₆ are chosen from alkenyl and alkyl groups comprising from 12 to 21 carbon atoms, for example, alkenyl and alkyl groups derived from tallow fatty acid, and wherein said R₅ and R₆ are chosen such that said quaternary ammonium salts of imidazolinium comprise at least one alkenyl group and at least one alkyl group, R₇ is methyl, and R₈ is hydrogen. Such products are, for example, (1) Quaternium-27 (International Cosmetic Ingredient Dictionary and Handbook, hereafter "CTFA", 1997), i.e., "Rewoquat" W75, W75PG, and W90, and (2) Quaternium-83 (CTFA 1997), i.e., "Rewoquat" W75HPG, which are sold by the company Witco.

Additionally, the quaternary ammonium salts are, for example, chosen from:

C) diquaternary ammonium salts of formula (VI):

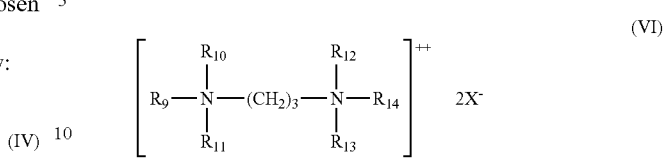

(VI)

in which:

R₉ is chosen from aliphatic groups comprising from 16 to 30 carbon atoms,

R₁₀, R₁₁, R₁₂, R₁₃ and R₁₄, which may be identical or different, are each chosen from a hydrogen atom and alkyl groups comprising from 1 to 4 carbon atoms, and $X^-$ is an anion chosen from halides, acetates, phosphates, nitrates and methyl sulfates. For example, such diquaternary ammonium salts can comprise propane tallow diammonium dichloride.

D) Quaternary ammonium salts comprising at least one ester function. The quaternary ammonium salts comprising at least one ester function that can be used according to the invention are, for example, those of formula (VII) below:

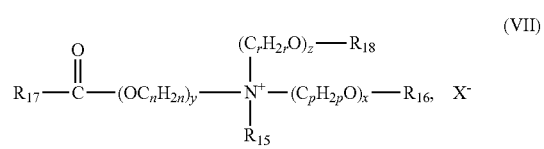

(VII)

in which:

R₁₅ is chosen from $C_1$-$C_6$ alkyl groups, $C_1$-$C_6$ hydroxyalkyl groups and $C_1$-$C_6$ dihydroxyalkyl groups;

R₁₆ is chosen from:

acyl groups of the following formula:

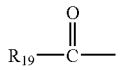

wherein R₁₉ is defined below, linear and branched, saturated and unsaturated, $C_1$-$C_{22}$ hydrocarbon-based groups, and a hydrogen atom;

R₁₈ is chosen from:

acyl groups of the following formula:

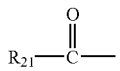

wherein R₂₁ is defined below, linear and branched, saturated and unsaturated, $C_1$-$C_6$ hydrocarbon-based groups, and a hydrogen atom;

R₁₇, R₁₉ and R₂₁, which may be identical or different, are each chosen from linear and branched, saturated and unsaturated, $C_7$-$C_{21}$ hydrocarbon-based groups;

n, p and r, which may be identical or different, are each chosen from integers ranging from 2 to 6;

y is chosen from integers ranging from 1 to 10;

x and z, which may be identical or different, are each chosen from integers ranging from 0 to 10;

$X^-$ is chosen from simple and complex, organic and inorganic anions;

provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups.

In one embodiment, the $R_{15}$ alkyl groups may be linear or branched and further, for example, linear.

For example, $R_{15}$ may be chosen from methyl, ethyl, hydroxyethyl and dihydroxypropyl groups and further for example from methyl and ethyl groups.

The sum x+y+z may for example range from 1 to 10.

When $R_{16}$ is chosen from linear and branched, saturated and unsaturated, $C_1$-$C_{22}$ hydrocarbon-based groups, $R_{16}$ may be long and comprise from 12 to 22 carbon atoms, or short and comprise from 1 to 3 carbon atoms.

When $R_{18}$ is chosen from linear and branched, saturated and unsaturated, $C_1$-$C_6$ hydrocarbon-based groups, $R_{18}$ may for example comprise from 1 to 3 carbon atoms.

$R_{17}$, $R_{19}$ and $R_{21}$, which may be identical or different, can each, for example, be chosen from linear and branched, saturated and unsaturated $C_{11}$-$C_{21}$ hydrocarbon-based groups, and for example from linear and branched, saturated and unsaturated, $C_{11}$-$C_{21}$ alkyl and alkenyl groups.

x and z, which may be identical or different, can for example each be chosen from 0 or 1.

y for example may be equal to 1.

n, p and r, which may be identical or different, can for example each be chosen from 2 and 3 and in one embodiment equal to 2.

The anion for example can be chosen from halides (chloride, bromide, and iodide) and alkyl sulfates, such as methyl sulfate. However, methanesulfonate, phosphate, nitrate, tosylate, anions derived from organic acids, such as acetate and lactate, and any other anions compatible with the ammonium comprising an ester function, may be used.

As a further example, the anion $X^-$ can be chosen from chloride and methyl sulfate.

Further examples of ammonium salts of formula (VII) are those in which:

$R_{15}$ is chosen from methyl and ethyl groups, x and y are equal to 1;

z is equal to 0 or 1;

n, p and r are equal to 2;

$R_{16}$ is chosen from:

acyl groups:

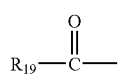

wherein $R_{19}$ is defined below, methyl, ethyl and $C_{14}$-$C_{22}$ hydrocarbon-based groups, and a hydrogen atom;

$R_{18}$ is chosen from:

acyl groups:

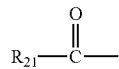

wherein $R_{21}$ is defined below, a hydrogen atom;

$R_{17}$, $R_{19}$ and $R_{21}$, which may be identical or different, are each chosen from linear and branched, saturated and unsaturated, $C_{13}$-$C_{17}$ hydrocarbon-based groups, such as from linear and branched, saturated and unsaturated $C_{13}$-$C_{17}$ alkyl and alkenyl groups.

The hydrocarbon-based groups can for example be linear.

Representative compounds of formula (VII) are chosen from diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (for example chloride and methyl sulfate). The acyl groups can for example comprise from 14 to 18 carbon atoms and can for example be obtained from plant oils, such as palm oil and sunflower oil. When the compound comprises several acyl groups, these groups, which may be independently chosen, may independently be identical or different.

These products are obtained, for example, by direct esterification of compounds chosen from triethanolamine, triisopropanolamine, alkyldiethanolamines and alkyldiisopropanolamines, which are optionally oxyalkylenated, with fatty acids or with fatty acid mixtures of plant or animal origin, and by transesterification of the methyl esters thereof. This esterification is followed by a quaternization using an alkylating agent such as alkyl halides (such as methyl and ethyl halides), dialkyl sulfates (for example dimethyl and diethyl sulfates), methyl methanesulfonate, methyl para-toluenesulfonate, glycol chlorohydrin and glycerol chlorohydrin.

Such compounds are sold, for example, under the names Dehyquart by the company Henkel, Stepanquat by the company Stepan, Noxamium by the company Ceca and Rewoquat WE 18 by the company Rewo-Witco.

One embodiment of the invention can comprise at least one quaternary ammonium monoester salt, at least one quaternary ammonium diester salt, and at least one quaternary ammonium triester salt, wherein said quaternary ammonium diester salt is, for example, present in a majority by weight.

Such an embodiment may comprise, for example, 15% to 30% by weight of acyloxyethyldihydroxyethylmethylammonium methyl sulfate, 45% to 60% by weight of diacyloxyethylhydroxyethylmethylammonium methyl sulfate, and 15% to 30% by weight of triacyloxyethylmethylammonium methyl sulfate, wherein said acyl groups comprise from 14 to 18 carbon atoms, and wherein said acyl groups are derived from palm oil that is optionally partially hydrogenated.

It is also possible to use the ammonium salts comprising at least one ester function, described in U.S. Pat. Nos. 4,874,554 and 4,137,180, the disclosures of which are incorporated by reference herein.

Representative quaternary ammonium salts of formula (IV) include tetraalkylammonium chlorides such as, for example, dialkyldimethylammonium chlorides and alkyltrimethylammonium chlorides, in which the alkyl group comprises from 12 to 22 carbon atoms, for example behenyltrimethylammonium chloride, distearyldimethylammonium chloride, cetyltrimethylammonium chloride, and benzyldimethylstearylammonium chloride, and, stearamidopropyldimethyl(myristyl acetate)ammonium chloride sold under the name "Cepharyl 70" by the company Van Dyk.

According to one embodiment of the invention, the quaternary ammonium salt can be behenyltrimethylammonium chloride.

The at least one additional ionic amphiphilic lipid chosen from cationic amphiphilic lipids and anionic amphiphilic lipids is generally present in the nanoemulsion of the invention in an amount ranging for example from 0.01% to 10% by weight relative to the total weight of the nanoemulsion, such as for example from 0.2% to 5% by weight relative to the total weight of the nanoemulsion.

The at least one oil that may be used in the nanoemulsion of the invention is, for example, chosen from:
- animal and plant oils formed by fatty acid esters of polyols, such as liquid triglycerides, for example sunflower oil, corn oil, soybean oil, avocado oil, jojoba oil, marrow oil, grapeseed oil, sesame oil, hazelnut oil, fish oils, glyceryl tricaprocaprylate, and plant and animal oils of formula $R_9COOR_{10}$ in which $R_9$ is chosen from fatty acid residues comprising from 7 to 29 carbon atoms and $R_{10}$ is chosen from linear and branched hydrocarbon-based chains comprising from 3 to 30 carbon atoms, such as alkyl and alkenyl, for example, purcellin oil and liquid jojoba wax;
- natural and synthetic essential oils such as, for example, eucalyptus oil, lavandin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
- synthetic oils;
- mineral oils such as hexadecane and liquid paraffin;
- halogenated oils, such as fluorocarbons, for example, fluoroamines (including for example perfluorotributylamine), fluorohydrocarbons (including for example perfluorodecahydronaphthalene), fluoroesters and fluoroethers;
- esters of at least one mineral acid and of at least one alcohol;
- liquid carboxylic acid esters; and
- volatile and non-volatile silicone oils.

Volatile and non-volatile silicone oils can for example be used in the presence of at least one non-silicon oil (oil which does not contain silicium atom). When used, the total amount of such silicone oils is generally an amount ranging for example from 5% to 50% by weight relative to the total weight of oils.

The synthetic oils can be chosen from for example polyolefins, such as poly-α-olefins and further such as:
- poly-α-olefins chosen from hydrogenated and non-hydrogenated polybutene poly-α-olefins, such as hydrogenated and non-hydrogenated polyisobutene poly-α-olefins.

One embodiment may comprise at least one isobutylene oligomer with a molecular weight of less than 1 000 and at least one polyisobutylene with a molecular weight of greater than 1 000 such as for example ranging from 1 000 to 15 000.

Representative carboxylic acid esters include monocarboxylic acid esters, dicarboxylic acid esters, tricarboxylic acid esters, and tetracarboxylic acid esters. The total number of carbons in the esters is generally equal to 10 or more, such as less than 100 and further such as less than 80.

The monocarboxylic acid esters can be chosen from saturated and unsaturated, linear and branched $C_1$-$C_{26}$ aliphatic acid monoesters derived from alcohols chosen from saturated and unsaturated, linear and branched $C_1$-$C_{26}$ aliphatic alcohols, wherein the total number of carbons in the esters is generally equal to 10 or more.

It is also possible to use esters derived from $C_4$-$C_{22}$ dicarboxylic acids and $C_1$-$C_{22}$ alcohols, esters derived from $C_4$-$C_{22}$ tricarboxylic acids and $C_1$-$C_{22}$ alcohols, esters derived from acids chosen from mono-, di-, and tricarboxylic acids and alcohols chosen from $C_2$-$C_{26}$ di-, tri-, tetra- and pentahydroxy alcohols.

Representative esters mentioned above which can be used include ethyl palmitate, isopropyl palmitate, 2-ethylhexyl palmitate, 2-octyldecyl palmitate, alkyl myristates such as isopropyl myristate, butyl myristate, cetyl myristate and 2-octyldodecyl myristate, hexyl stearate, butyl stearate, isobutyl stearate; dioctyl malate, hexyl laurate, 2-hexyldecyl laurate, isononyl isononanate, and cetyl octanoate.

The at least one oil of the nanoemulsions in accordance with the invention is generally present in an amount ranging for example from 2% to 40% by weight relative to the total weight of the nanoemulsion, such as for example from 4% to 30% by weight relative to the total weight of the nanoemulsion, and further such as for example from 8% to 20% by weight relative to the total weight of the nanoemulsion.

According to one embodiment, such as for example an embodiment of the invention that is used for hair compositions, the compositions according to the invention can also comprise at least one aminosilicone.

Hereinabove and hereinbelow, the terms at least one "silicone" and "polysiloxane" are synonymous and are understood to include linear and cyclic, branched and crosslinked organosilicon polymers and organosilicon oligomers of variable molecular weight, obtained by polymerization and/or polycondensation of suitably functionalized silanes, and which comprise repeating units in which the silicon atoms are connected together by oxygen atoms (siloxane bond ≡Si—O—Si≡) and are optionally substituted with at least one hydrocarbon-based group, which is bonded by way of a carbon atom of said hydrocarbon-based group to said silicon atoms. The most common hydrocarbon-based groups are alkyl groups, such as $C_1$-$C_{10}$ alkyl groups and further such as methyl, fluoroalkyl groups, aryl groups, such as phenyl, and alkenyl groups such as vinyl; other groups that can be bonded, either directly or by way of a hydrocarbon-based linking group, to the siloxane chain can be chosen from a hydrogen atom, halogens, such as chlorine, bromine and fluorine, thiols, alkoxy groups, polyoxyalkylene groups, such as polyoxyethylene and polyoxypropylene, polyether groups, hydroxyl, hydroxyalkyl groups, amide groups, acyloxy groups, acyloxyalkyl groups, amphoteric groups, betaine groups, anionic groups such as carboxylates, thioglycolates, sulfosuccinates, thiosulfates, phosphates and sulfates, this list obviously being in no way limiting (so-called "organomodified" silicones).

According to the invention, the term at least one "aminosilicone" means any silicone comprising at least one amine chosen from primary, secondary, and tertiary amines or at least one quaternary ammonium group. Mention may thus be made of:

(a) polysiloxanes referred to in the CTFA dictionary as "amodimethicone" of formula (IV):

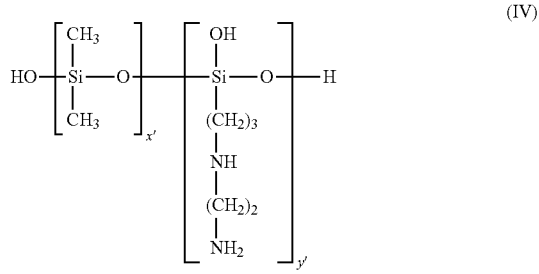

(IV)

in which x' and y' are integers chosen such that generally the weight-average molecular weight of said aminosilicone ranges from 5 000 to 500 000 approximately;

(b) said at least one aminosilicone corresponding to formula (V):

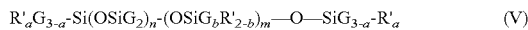

$R'_a G_{3-a}\text{-Si}(OSiG_2)_n\text{-}(OSiG_b R'_{2-b})_m\text{—O—}SiG_{3-a}\text{-}R'_a$ (V)

in which:

G is chosen from a hydrogen atom, a phenyl group. OH group, and $C_1$-$C_8$ alkyl groups, for example methyl, a is an integer ranging from 0 to 3, and in one embodiment a is 0, b is chosen from 0 and 1, and in one embodiment b is 1, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;

R' is a monovalent group of formula —$C_q H_{2q} L$ in which q is a number from 2 to 8 and L is an optionally quaternized amine group chosen from the groups:

NR"—$CH_2$—$CH_2$—N(R")$_2$,
N(R")$_2$,
N$^+$(R")$_3$A$^-$,
N$^+$H(R")$_2$A$^-$,
N$^+$H$_2$(R")A$^-$, and
N(R")—$CH_2$—$CH_2$—N$^+$R"H$_2$A$^-$, in which R" can be chosen from a hydrogen atom, phenyl groups, benzyl groups, and saturated monovalent hydrocarbon-based groups, such as for example an alkyl group comprising from 1 to 20 carbon atoms, and A$^-$ is chosen from halide ions such as, for example, fluoride, chloride, bromide and iodide.

One aminosilicone of said at least one aminosilicone corresponding to formula (V) is known as "trimethylsilylamodimethicone" of formula (VI):

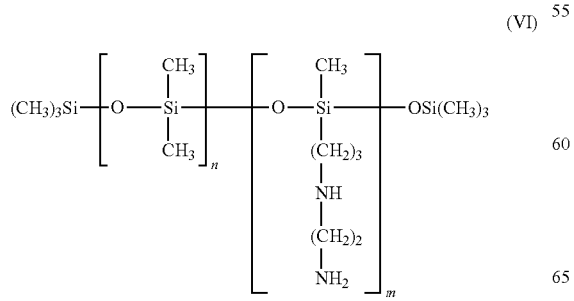

(VI)

in which:

m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10.

Such polymers are described, for example in patent application EP-A-95238, the disclosure of which is incorporated herein by reference.

Additional said at least one aminosilicone of the invention include:

(c) said at least one aminosilicone of formula (VII):

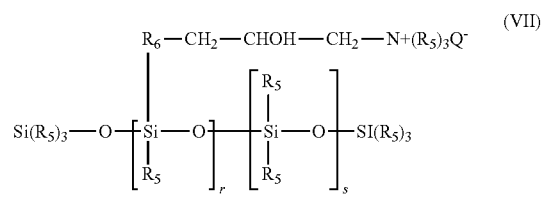

(VII)

in which:

$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;

$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;

Q$^-$ is an anion that can be for example chosen from halide ions, such as chloride, and organic acid salts (such as acetate);

r is an average statistical value ranging from 2 to 20, such as from 2 to 8;

s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:

d) quaternary ammonium silicones of formula (VIIb):

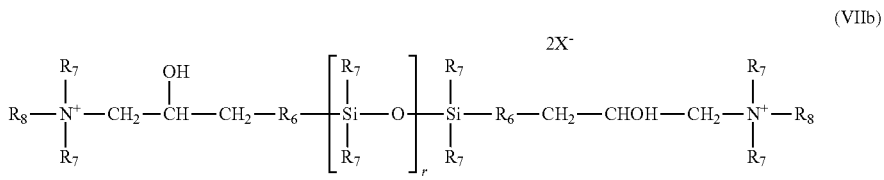

(VIIb)

in which:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;

$R_6$ is chosen from divalent hydrocarbon-based groups, such as divalent $C_1$-$C_{18}$ alkylene groups and divalent $C_1$-$C_{18}$ alkylenoxy, for example $C_1$-$C_8$, group connected to the Si by an SiC bond;

$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—$NHCOR_7$;

$X^-$ is an anion such as a halide ion, in particular chloride, or an organic acid salt (acetate, etc.);

r represents an average statistical value from 2 to 200, such as for example from 5 to 100.

Such silicones are described, for example, in application EP-A-0 530 974, the disclosure of which is incorporated by reference herein.

Silicones falling within this class are the silicones sold by the company Goldschmidt under the names Abil Quat 3270, Abil Quat 3272 and Abil Quat 3474.

According to the invention, said at least one aminosilicone can be present in at least one form chosen from the form of an oil, the form of a solution chosen from aqueous, alcoholic and aqueous-alcoholic solutions, the form of a dispersion, and the form of an emulsion.

In one embodiment, the aminosilicones can be present in the form of an emulsion, such as emulsions chosen from microemulsions and nanoemulsions.

The product sold under the name "Cationic Emulsion DC 929" by Dow Corning, which comprises, besides amodimethicone, a cationic surfactant derived from tallow fatty acids, referred to as Tallotrimonium (CTFA), in combination with a nonionic surfactant, known under the name "Nonoxynol 10", can be used for example.

The product sold under the name "Cationic Emulsion DC 939" by Dow Corning, which comprises, besides amodimethicone, a cationic surfactant, trimethylcetylammonium chloride, in combination with a nonionic surfactant, trideceth-12, can also be used for example.

Another commercial product which can be used according to the invention is the product sold under the name "Dow Corning Q2 7224" by Dow Corning, comprising, in combination, the trimethylsilylamodimethicone of formula (IV), a nonionic surfactant of formula: $C_8H_{17}$—$C_6H_4$—$(OCH_2CH_2)_n$—OH in which n=40, also known as octoxynol-40, another nonionic surfactant of formula: $C_{12}H_{25}$—$(OCH_2CH_2)_n$—OH in which n=6, also known as isolaureth-6, and glycol.

The at least one aminosilicone is generally present in an amount ranging for example from 0.05% to 10% by weight relative to the total weight of the nanoemulsion, such as for example from 0.1% to 5% by weight relative to the total weight of the nanoemulsion, and further such as from 0.3% to 3% by weight relative to the total weight of the nanoemulsion.

The nanoemulsions in accordance with the present invention may comprise at least one solvent, for example, if desired, to improve the transparency of the formulation.

The at least one solvent can be for example chosen from:
$C_1$-$C_8$ alcohols such as ethanol;
glycols such as glycerol, propylene glycol, 1,3-butylene glycol, dipropylene glycol, polyethylene glycols comprising from 4 to 16, for example, from 8 to 12 ethylene oxide units.

The at least one solvent such as those mentioned above are generally present in the nanoemulsions of the invention in an amount ranging for example from 0.01% to 30% by weight relative to the total weight of the nanoemulsion.

In addition, the use of the alcohols as defined above, in an amount of at least 5% by weight relative to the total weight of the nanoemulsion, such as for example at least 15% by weight relative to the total weight of the nanoemulsion, may make it possible for one skilled in the art to obtain nanoemulsions without a preserving agent.

The nanoemulsions of the invention can additionally comprise at least one active agent chosen from water-soluble, water-dispersible, and liposoluble cosmetic active agents and water-soluble, water-dispersible, and liposoluble dermopharmaceutical active agents. The liposoluble active agents are present in the oily globules of the nanoemulsion, while the water-soluble and water-dispersible active agents are present in the aqueous phase of the nanoemulsion. Non-limiting examples of said at least one active agent include vitamins and derivatives thereof, such as vitamin E, vitamin E acetate, vitamin C and its esters, B vitamins, vitamin A alcohol and vitamin A retinol, vitamin A acid and vitamin A retinoic acid and its derivatives, provitamins such as panthenol, vitamin A palmitate, niacinamide, ergocalciferol, antioxidants, essential oils, wetting agents, silicone and non-silicone sunscreens, preserving agents, sequestering agents, softeners, dyes, viscosity modifiers, foam modifiers, foam stabilizers, nacreous agents, pigments, moisturizers, antidandruff agents, antiseborrhoeic agents, proteins, ceramides, pseudoceramides, fatty acids comprising linear and branched $C_{16}$-$C_{40}$ chains, such as 18-methyl eicosanoic acid, plasticizers, hydroxy acids, electrolytes, polymers, such as cationic polymers, and fragrances.

The oil globules in the nanoemulsions of the invention can for example have an average size ranging from 20 nm to 150 nm, such as for example from 30 nm to 100 nm and further such as for example from 40 nm to 80 nm.

The nanoemulsions according to the invention generally have a transparent to blueish appearance. Their transparency is measured by a coefficient of transmittance at 600 nm ranging for example from 10% to 90%, or alternatively by a turbidity ranging for example from 60 NTU to 600 NTU such as for example from 70 NTU to 400 NTU, the turbidity being measured using a Hach Model 2100 P portable turbidimeter.

The nanoemulsions of the invention may be obtained by a process comprising:
(1) combining the aqueous phase and the oily phase by mixing with vigorous stirring at a temperature of less than 45° C.,
(2) homogenizing said combination at a pressure of greater than $5 \times 10^7$ Pa such as ranging for example from $6 \times 10^7$ to $18 \times 10^7$ Pa.

Such a process makes it possible to produce, at room temperature, nanoemulsions that tend to be compatible with heat-sensitive active compounds and that can comprise large amounts of oils, such as fragrances comprising fatty substances, whereby the possibility of denaturing such oils tends to be reduced.

Another subject of the invention is a composition for topical use such as a composition chosen from cosmetic compositions and dermopharmaceutical compositions, wherein said composition for topical use comprises a nanoemulsion comprising oil globules with an average size of less than 150 nm comprising at least one oil, at least one amphiphilc lipid, and at least one nonionic polymer comprising at least one hydrophobic block and at least one hydrophilic block.

The compositions in accordance with the invention may be used for at least one use chosen from washing keratin materials, cleaning keratin materials, and removing make-up from keratin materials such as the hair, the skin, the eyelashes, the eyebrows, the nails and mucous membranes.

The compositions of the invention can for example be in forms chosen from shampoos, rinse-out conditioners, leave-in conditioners, permanent-waving compositions, relaxing compositions, dyeing compositions, bleaching compositions, compositions to be applied before a procedure chosen from dyeing, bleaching, permanent-waving and relaxing the hair, compositions to be applied after a procedure chosen from dyeing, bleaching, permanent-waving and relaxing the hair, and compositions to be applied between the two steps of a procedure chosen from permanent-waving and relaxing the hair.

The compositions may also be in at least one form chosen from hairsetting lotions, blow-drying lotions, fixing compositions (lacquers), and styling compositions such as, for example, gels and mousses.

The compositions can be packaged in various forms chosen from vaporizers, pump-dispenser bottles and aerosol containers in order to ensure application of the composition in vaporized form or in the form of a mousse. Such packaging forms are indicated, for example, when it is desired to obtain a spray, a lacquer or a mousse for fixing or treating the hair.

When the composition according to the invention is packaged in aerosol form in order to obtain an aerosol lacquer or mousse, it comprises at least one propellant which may be chosen from volatile hydrocarbons such as n-butane, propane, isobutane and pentane, chlorohydrocarbons, fluorohydrocarbons, carbon dioxide, nitrous oxide, dimethyl ether, nitrogen and compressed air.

The compositions in accordance with the invention may be used to care for a keratin material chosen from for example hair, body skin, facial skin, eyelashes, eyebrows, nails, and mucous membranes.

The compositions in accordance with the invention may be used to make up a keratin material chosen from for example hair, body skin, facial skin, eyelashes, eyebrows, nails, and mucous membranes.

Another subject of the invention is a cosmetic product base, such as for example lotions, sera, milks, creams and eaux de toilette for caring, making-up, or removing make-up from a keratin material, such as for example body skin, facial skin, the scalp, the hair, the nails, the eyelashes, the eyebrows, and mucous membranes, and further such as for example the lips, wherein said cosmetic product base comprises at least one nanoemulsion comprising oil globules with an average size of less than 150 nm comprising at least one oil, at least one amphiphilc lipid, and at least one nonionic polymer comprising at least one hydrophobic block and at least one hydrophilic block.

Another subject of the invention relates to a non-therapeutic care process for a keratin material comprising applying a nanoemulsion comprising oil globules with an average size of less than 150 nm comprising at least one oil, at least one amphiphilc lipid, and at least one nonionic polymer comprising at least one hydrophobic block and at least one hydrophilic block to said keratin material chosen from for example the skin, the hair, the eyelashes, the eyebrows, the nails, mucous membranes and the scalp.

Concrete examples illustrating the invention are indicated below without however exhibiting a limiting character.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

EXAMPLES

The following procedure was used:
in a first phase A, the nonionic and cationic amphiphilic lipids were homogenized with the oil and the lipophilic (liposoluble) active agents and adjuvants at a temperature of about 80° C. and the mixture was allowed to cool to 50° C., with stirring using a doctor blade;
the fragrance, the preserving agent and the cyclomethicone were then added, and cooling was continued down to 30° C.;
in a second phase B, 65% of the water and the water-soluble and water-dispersible active agents and adjuvants were mixed in at a temperature of 20 to 30° C.;
a third phase C was prepared containing 35% of the water and the nonionic polymer. This phase was melted at 80° C. and was then cooled to 60° C.;
phases A and B were then mixed together using a turbomixer homogenizer and the mixture was then homogenized using a high-pressure homogenizer such as a Soavi-Niro machine at a pressure of 1 200 bar, in 4 homogenization runs, while keeping the temperature of the product below about 35° C.

Phase C was added with stirring, at room temperature.

Example 1

A conditioner to be rinsed off comprising the composition below was prepared:

Phase A:

| | |
|---|---|
| PEG-400 isostearate as sold by Unichema | 2 g |
| Behenyltrimethylammonium chloride containing 80% AM (Genamin DDMP from Goldschmidt) | 2 g (1.6 g AM) |
| Avocado oil | 5.25 g |
| Jojoba oil | 5.25 g |
| Fragrance | qs |
| Preserving agent | qs |
| Cyclopentadimethylsiloxane (DC245 from Dow Corning) | 3.5 g |

Phase B:

| | |
|---|---|
| Trimethylsilylamodimethicone microemulsion containing 20% AM, sold under the name SME 253 by General Electric | 6 g (1.2 g AM) |
| Dipropylene glycol | 10 g |
| Sorbitan monolaurate oxyethylenated with 20 mol of ethylene oxide (Tween 20 from ICI) | 0.5 g |
| Demineralized water | 38 g |
| Glycerol | 5 g |

Phase C:

| | |
|---|---|
| Polycondensate comprising at least one polyethylene glycol containing 150 or 180 mol of ethylene oxide, stearyl alcohol and methylenebis(4-cyclohexyl isocyanate) (SMDI) at a concentration of 15% by weight in a matrix of maltodextrin (4%) and water (81%) (Aculyn 46 from Rohm & Haas) | 5 g (0.75 g AM) |
| Water | 21 g |

A nanoemulsion in which the size of the oil globules is about 63 nm was obtained. This composition was stable on storage for 2 months at room temperature and at 45° C.

The composition had a turbidity of 318 NTU and a viscosity of 1 300 mPa·s (cP).

The turbidity was measured using a Hach Model 2100 P turbidimeter at 25° C., in NTU units (Nephelometric turbidity units). (The machine was calibrated with formazine).

The viscosity was measured using a Rheomat 108 rheometer with a shear rate of 200 s$^{-1}$ at 25° C. (spindle 4).

The hair treated with this composition was easy to disentangle, soft and shiny.

If the Aculyn 46 is replaced with 1% AM by weight of Carbopol Ultrez, a composition which is not thickened, not transparent (turbidity>1 000 NTU) and not stable on storage is obtained.

Example 2

The composition below was prepared:

Phase A:

| | |
|---|---|
| PEG-400 isostearate | 4.5% |
| Disodium acylglutamate | 0.5% |
| Isopropyl myristate | 5% |
| Isocetyl stearate | 10% |

Phase B:

| | |
|---|---|
| Dipropylene glycol | 10% |
| Glycerol | 5% |
| Distilled water | 45% |

Phase C:

| | |
|---|---|
| SER-AD FX 1100 (Servo Delden) | 0.5% |
| Distilled water | 19.5% |

Turbidity/viscosity 25° C. at t=0 without gelling agent: 149 NTU/liquid like water Turbidity/viscosity 25° C. at t=0: 150 NTU/17.1 Pa·s (spindle 4)

Turbidity/viscosity 25° C. at t=1 month: 152 NTU/16.4 Pa·s (spindle 4)

Turbidity/viscosity 25° C. at t=2 months: 155 NTU/15.4 Pa·s (spindle 4)

(viscosity measurements carried out using an Epprecht 180 rheometer at 25° C.)

For this example, total stability of the turbidity and good stability of the viscosity over a period of 2 months were noted.

Examples 3, 4, 5, and 6

The compositions below were prepared:

| | 3 | 4 | 5 | 6 |
|---|---|---|---|---|
| Phase A: | | | | |
| PEG-400 isostearate | 4.5% | 4.5% | 4.5% | 4.5% |
| Disodium acylglutamate | 0.5% | 0.5% | 0.5% | 0.5% |
| Isopropyl myristate | 5% | 5% | 5% | 5% |
| Isocetyl stearate | 10% | 10% | 10% | 10% |
| Phase B: | | | | |
| Dipropylene glycol | 10% | 10% | 10% | 10% |
| Glycerol | 5% | 5% | 5% | 5% |
| Distilled water | 45% | 45% | 45% | 45% |
| Phase C: | | | | |
| Rheolate 205 | 0.5% | — | — | — |
| Esaflor HM 22 | — | 0.1% | 0.75% | — |

-continued

| | | | | |
|---|---|---|---|---|
| Natrosol Grade Plus 330 | — | — | — | 0.5% |
| Distilled water qs | 100% | 100% | 100% | 100% |

| | Ex. 3 | Ex. 4 | Ex. 5 | Ex. 6 |
|---|---|---|---|---|
| Turbidity | 177 NTU | 201 NTU | 377 NTU | 362 NTU |
| Viscosity in Pa · s | 9 (spindle 4) | 0.061 (spindle 3) | 0.18 (spindle 3) | 0.15 (spindle 3) |

Viscosity measurements carried out using an Epprecht 180 rheometer at 25° C.)

What is claimed is:

1. An oil-in-water nanoemulsion comprising:

a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and at least one ionic amphiphilic lipid chosen from cationic amphiphilic lipids and anionic amphiphilic lipids chosen from:

alkaline salts of dicetyl phosphate and of dimyristyl phosphate;

alkaline salts of cholesteryl sulfate;

alkaline salts of cholesteryl phosphate;

lipoamino acids and salts thereof;

sodium salts of phosphatidic acid;

phospholipids; and alkylsulfonic derivatives of formula:

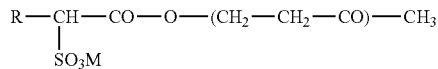

in which R, which may be identical or different in embodiments wherein more than one of said alkylsulfonic derivative is used, is chosen from $C_{16}$-$C_{22}$ alkyl groups, and M is chosen from alkali metals and alkaline-earth metals, wherein the at least one cationic amphiphilic lipid chosen from:

A) quaternary ammonium salts of formula (IV):

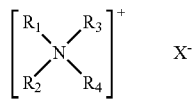

in which:

$R_1$, $R_2$, $R_3$ and $R_4$, which may be identical or different, are each chosen from:

linear and branched aliphatic groups comprising from 1 to 30 carbon atoms and optionally comprising atoms chosen from hetero and halogen atoms, and aromatic groups, and $X^-$ is an anion chosen from halides, phosphates, acetates, lactates, ($C_2$-$C_6$)alkyl sulfates, alkyl sulfonates, and alkylaryl sulfonates;

B) quaternary ammonium salts of imidazolinium of formula (V):

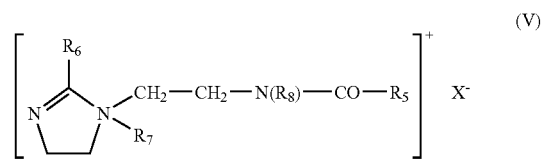

in which:

$R_5$ is chosen from alkenyl and alkyl groups comprising from 8 to 30 carbon atoms, $R_6$ is chosen from a hydrogen atom, $C_1$-$C_4$ alkyl groups, and alkenyl and alkyl groups comprising from 8 to 30 carbon atoms, $R_7$ is chosen from $C_1$-$C_4$ alkyl groups, $R_8$ is chosen from a hydrogen atom and $C_1$-$C_4$ alkyl groups, and $X^-$ is an anion chosen from halides, phosphates, acetates, lactates, alkyl sulfates, alkyl sulfonates, and alkylaryl sulfonates;

C) diquaternary ammonium salts of formula (VI):

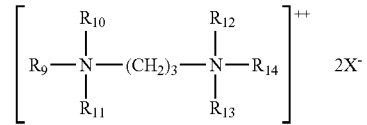

in which:

$R_9$ is chosen from aliphatic groups comprising from 16 to 30 carbon atoms, $R_{10}$, $R_{11}$, $R_{12}$, $R_{13}$ and $R_{14}$, which may be identical or different, are each chosen from a hydrogen atom and alkyl groups comprising from 1 to 4 carbon atoms, and $X^-$ is an anion chosen from halides, acetates, phosphates, nitrates and methyl sulfates; and D) quaternary ammonium salts comprising at least one ester function chosen from said quaternary ammonium salts of formula (VII):

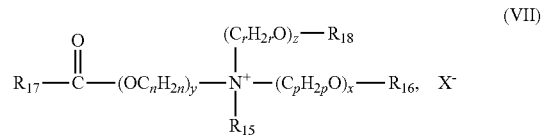

in which:

$R_{15}$ is chosen from $C_1$-$C_6$ alkyl groups, $C_1$-$C_6$ hydroxyalkyl groups and $C_1$-$C_6$ dihydroxyalkyl groups;

$R_{16}$ is chosen from:
acyl groups of the following formula:

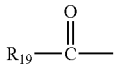

wherein $R_{19}$ is chosen from:
linear and branched, saturated and unsaturated, $C_1$-$C_{22}$ hydrocarbon-based groups, and
a hydrogen atom;
$R_{18}$ is chosen from:
acyl groups of the following formula:

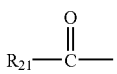

wherein $R_{21}$ chosen from:
linear and branched, saturated and unsaturated, $C_1$-$C_6$ hydrocarbon-based groups, and
a hydrogen atom;
$R_{17}$, $R_{19}$ and $R_{21}$, which may be identical or different, are each chosen from linear and branched, saturated and unsaturated, $C_7$-$C_{21}$ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network,
with the proviso that the oil-in-water nanoemulsion does not comprise aminosilicone.

2. A nanoemulsion according to claim 1, wherein said at least one oil and said at least one amphiphilic lipid are present in amounts wherein the weight ratio of the amount of said at least one oil to the amount of said at least one amphiphilic lipid ranges from 1:1 to 10:1.

3. A nanoemulsion according to claim 2, wherein said weight ratio ranges from 1.2:1 to 6:1.

4. A nanoemulsion according to claim 1, wherein said oil globules have an average size ranging from 30 nm to 100 nm.

5. A nanoemulsion according to claim 1, wherein said at least one nonionic polymer is chosen from water-soluble nonionic polymers and water-dispersible nonionic polymers.

6. A nanoemulsion according to claim 1, wherein said at least one nonionic polymer comprises at least two hydrophobic blocks.

7. A nanoemulsion according to claim 1, wherein said at least one hydrophobic block is chosen from fatty chains comprising from 6 to 30 carbon atoms, divalent aliphatic groups, divalent cycloaliphatic groups and divalent aromatic groups.

8. A nanoemulsion according to claim 7, wherein said fatty chains comprising from 6 to 30 carbon atoms are chosen from alkyl chains, arylalkyl chains, alkylaryl chains and alkenyl chains.

9. A nanoemulsion according to claim 1, wherein said at least one hydrophobic block and said at least one hydrophilic block are bonded with at least one linking group chosen from ester, ether, urea, amide and urethane linkers.

10. A nanoemulsion according to claim 1, wherein said at least one hydrophilic block and said at least one hydrophobic block are present in amounts wherein the weight ratio of the amount of said at least one hydrophilic block to the amount of said at least one hydrophobic block ranges from 10:1 to 1000:1.

11. A nanoemulsion according to claim 1, wherein said polyether-polyurethanes comprise at least two lipophilic hydrocarbon chains comprising from 6 to 30 carbon atoms, separated by a hydrophilic block, wherein said hydrocarbon chains are chosen from pendant chains and chains at the end of a hydrophilic block.

12. A nanoemulsion according to claim 1, wherein said polyether-polyurethanes are multiblock polymers.

13. A nanoemulsion according to claim 1, wherein said polyether-polyurethanes are triblock polymers.

14. A nanoemulsion according to claim 1, wherein said at least one nonionic polymer is present in an amount ranging from 0.01% to 10% by weight relative to the total weight of the composition.

15. A nanoemulsion according to claim 14, wherein said at least one nonionic polymer is present in an amount ranging from 0.1% to 5% by weight relative to the total weight of the composition.

16. A nanoemulsion according to claim 1, wherein said at least one amphiphilic lipid is chosen from nonionic amphiphilic lipids and anionic amphiphilic lipids.

17. A nanoemulsion according to claim 16, wherein said nonionic amphiphilic lipids are chosen from:
1/—silicone surfactants,
2/—nonionic amphiphilic lipids that are fluid at a temperature of less than or equal to 45° C. chosen from esters formed from (i) at least one polyol chosen from polyethylene glycol comprising from 1 to 60 ethylene oxide units, sorbitan, glycerol comprising from 2 to 30 ethylene oxide units, and polyglycerols comprising from 2 to 15 glycerol units, and (ii) at least one fatty acid comprising at least one alkyl chain chosen from saturated and unsaturated, linear and branched $C_8$-$C_{22}$ alkyl chains,
3/—mixed esters derived from (i) at least one fatty acid, at least one carboxylic acid, and glycerol, and mixed esters derived from (ii) at least one fatty alcohol, at least one carboxylic acid, and glycerol, wherein said at least one carboxylic acid is chosen from α-hydroxy acids and succinic acid,
4/—fatty acid esters of sugars and fatty alcohol ethers of sugars,
5/—surfactants that are solid at a temperature of less than or equal to 45° C. chosen from fatty esters of glycerol, fatty esters of sorbitan, oxyethylenated fatty esters of sorbitan, ethoxylated fatty ethers, and ethoxylated fatty esters, and
6/—block copolymers of ethylene oxide (A) and of propylene oxide (B).

18. A nanoemulsion according to claim 16, wherein said nonionic amphiphilic lipids are chosen from:
polyethylene glycol isostearate comprising 8 ethylene oxide units,
diglyceryl isostearate, polyglyceryl monolaurate, polyglyceryl monostearate, and polyglyceryl distearate which comprise 10 glycerol units,
sorbitan oleate, and
sorbitan isostearate.

19. A nanoemulsion according to claim 16, wherein said anionic amphiphilic lipids are chosen from:
alkyl ether citrates,
alkoxylated alkenyl succinates,
alkoxylated glucose alkenyl succinates, and
alkoxylated methylglucose alkenyl succinates.

20. A nanoemulsion according to claim 1, wherein said at least one amphiphilic lipid is present in an amount ranging from 0.2% to 15% by weight relative to the total weight of the nanoemulsion.

21. A nanoemulsion according to claim 20, wherein said at least one amphiphilic lipid is present in an amount ranging from 1% to 8% by weight relative to the total weight of the nanoemulsion.

22. A nanoemulsion according to claim 1, wherein said lipoamino acids and salts thereof are chosen from monosodium and disodium acylglutamates.

23. A nanoemulsion according to claim 22, wherein said lipoamino acids and salts thereof are chosen from the disodium salt of N-stearoyl-L-glutamic acid.

24. A nanoemulsion according to claim 1, wherein said R is chosen from $C_{16}H_{33}$ and $C_{18}H_{37}$ groups.

25. A nanoemulsion according to claim 1, wherein said M is sodium.

26. A nanoemulsion according to claim 1, wherein said aromatic groups are chosen from aryl and alkylaryl groups.

27. A nanoemulsion according to claim 1, wherein said hetero atoms are chosen from oxygen, nitrogen, and sulfur.

28. A nanoemulsion according to claim 1, wherein said aliphatic groups are chosen from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate, and hydroxyalkyl groups comprising from 1 to 30 carbon atoms.

29. A nanoemulsion according to claim 1, wherein said alkenyl and alkyl groups comprising from 8 to 30 carbon atoms are chosen from groups derived from tallow fatty acid.

30. A nanoemulsion according to claim 1, wherein said diquaternary ammonium salts of formula (VI) comprise propane tallow diammonium dichloride.

31. A nanoemulsion according to claim 1, wherein said $R_{15}$ alkyl groups are chosen from linear and branched alkyl groups.

32. A nanoemulsion according to claim 31, wherein said $R_{15}$ alkyl groups are chosen from linear alkyl groups.

33. A nanoemulsion according to claim 32, wherein said $R_{15}$ alkyl groups are chosen from methyl, ethyl, hydroxyethyl and dihydroxypropyl groups.

34. A nanoemulsion according to claim 33, wherein said $R_{15}$ alkyl groups are chosen from methyl and ethyl groups.

35. A nanoemulsion according to claim 1, wherein said sum of x+y+z ranges from 1 to 10.

36. A nanoemulsion according to claim 1, wherein when said $R_{16}$ is chosen from linear and branched, saturated and unsaturated, $C_1$-$C_{22}$ hydrocarbon-based groups, $R_{16}$ is chosen from hydrocarbon-based groups comprising from 12 to 22 carbon atoms, and hydrocarbon-based groups comprising from 1 to 3 carbon atoms.

37. A nanoemulsion according to claim 1, wherein when said $R_{18}$ is chosen from linear and branched, saturated and unsaturated, $C_1$-$C_6$ hydrocarbon-based groups, $R_{18}$ comprises from 1 to 3 carbon atoms.

38. A nanoemulsion according to claim 37, wherein said $R_{18}$ comprises from 1 to 3 carbon atoms.

39. A nanoemulsion according to claim 1, wherein said $R_{17}$, $R_{19}$ and $R_{21}$, which may be identical or different, are each chosen from linear and branched, saturated and unsaturated $C_{11}$-$C_{21}$ hydrocarbon-based groups.

40. A nanoemulsion according to claim 39, wherein said $R_{17}$, $R_{19}$ and $R_{21}$, which may be identical or different, are each chosen from linear and branched, saturated and unsaturated, $C_{11}$-$C_{21}$ alkyl and alkenyl groups.

41. A nanoemulsion according to claim 1, wherein said x and z, which may be identical or different, are each chosen from 0 or 1.

42. A nanoemulsion according to claim 1, wherein said y is equal to 1.

43. A nanoemulsion according to claim 1, wherein said n, p and r, which may be identical or different, are each chosen from 2 and 3.

44. A nanoemulsion according to claim 43, wherein said n, p and r, which may be identical or different, are each equal to 2.

45. A nanoemulsion according to claim 1, wherein said anion is chosen from halides and alkyl sulfates.

46. A nanoemulsion according to claim 45, wherein said halides are chosen from chloride, bromide, and iodide.

47. A nanoemulsion according to claim 45, wherein said alkyl sulfates are chosen from methyl sulfate.

48. A nanoemulsion according to claim 1, wherein said anion is chosen from methanesulfonate, phosphate, nitrate, and tosylate.

49. A nanoemulsion according to claim 48, wherein said anion is chosen from anions derived from organic acids.

50. A nanoemulsion according to claim 1, wherein the at least one cationic amphiphilic lipid of formula (IV) is chosen from tetraalkylammonium chlorides.

51. A nanoemulsion according to claim 50, wherein said tetraalkylammonium chlorides are chosen from dialkyldimethylammonium chlorides, and alkyltrimethylammonium chlorides, wherein said alkyl portion comprises from 12 to 22 carbon atoms.

52. A nanoemulsion according to claim 1, wherein the at least one cationic amphiphilic lipid of formula (IV) is chosen from behenyltrimethylammonium chloride, distearyldimethylammonium chloride, cetyltrimethylammonium chloride, benzyldimethylstearylammonium chloride and stearamidopropyldimethyl(myristyl acetate)ammonium chloride.

53. A nanoemulsion according to claim 1, wherein the at least one cationic amphiphilic lipid of formula (IV) is chosen from behenyltrimethylammonium salts and stearamidopropyldimethyl(myristyl acetate)ammonium salts.

54. A nanoemulsion according to claim 1, wherein said at least one ionic amphiphilic lipid chosen from cationic amphiphilic lipids and anionic amphiphilic lipids is present in said nanoemulsion in an amount ranging from 0.01% to 10% by weight relative to the total weight of the nanoemulsion.

55. A nanoemulsion according to claim 54, wherein said at least one ionic amphiphilic lipid chosen from cationic amphiphilic lipids and anionic amphiphilic lipids is present in said nanoemulsion in an amount ranging from 0.2% to 5% by weight relative to the total weight of the nanoemulsion.

56. A nanoemulsion according to claim 1, wherein said at least one oil is chosen from plant oils, animal oils, synthetic oils, mineral oils, halogenated oils, esters of a mineral acid and of an alcohol, liquid carboxylic acid esters and silicones.

57. A nanoemulsion according to claim 1, wherein said at least one oil is present in an amount ranging from 2% to 40% by weight relative to the total weight of the nanoemulsion.

58. A nanoemulsion according to claim 57, wherein said at least one oil is present in an amount ranging from 4% to 30% by weight relative to the total weight of the nanoemulsion.

59. A nanoemulsion according to claim 1 further comprising at least one active agent chosen from water-soluble, water-dispersible, and liposoluble cosmetic active agents and water-soluble, water-dispersible, and liposoluble dermopharmaceutical active agents.

60. A nanoemulsion according to claim 1, wherein said nanoemulsion has a turbidity ranging from 60 NTU to 600 NTU.

61. A composition for topical use chosen from cosmetic compositions and dermopharmaceutical compositions, wherein said composition for topical use comprises a nanoemulsion comprising:
a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and
at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

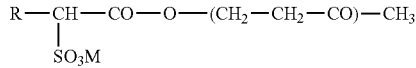

in which R, which may be identical or different in embodiments wherein more than one of said alkylsulfonic derivative is used is chosen from $C_{16}$-$C_{22}$ alkyl groups and M is chosen from alkali metals and alkaline-earth metals,
wherein the at least one cationic amphiphilic lipid chosen from:
A) quaternary ammonium salts of formula (IV):

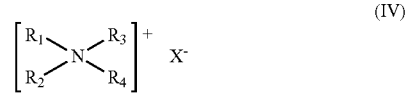

in which:
$R_1$, $R_2$, $R_3$ and $R_4$, which may be identical or different, are each chosen from:
linear and branched aliphatic groups comprising from 1 to 30 carbon atoms and optionally comprising atoms chosen from hetero and halogen atoms, and aromatic groups, and
$X^-$ is an anion chosen from halides, phosphates, acetates, lactates, ($C_2$-$C_6$)alkyl sulfates, alkyl sulfonates, and alkylaryl sulfonates;

B) quaternary ammonium salts of imidazolinium of formula (V):

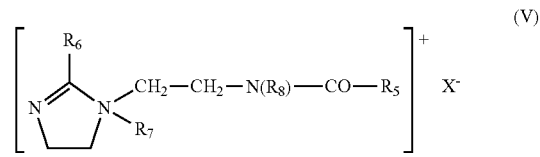

in which:
$R_5$ is chosen from alkenyl and alkyl groups comprising from 8 to 30 carbon atoms,
$R_6$ is chosen from a hydrogen atom, $C_1$-$C_4$ alkyl groups, and alkenyl and alkyl groups comprising from 8 to 30 carbon atoms,
$R_7$ is chosen from $C_1$-$C_4$ alkyl groups,
$R_8$ is chosen from a hydrogen atom and $C_1$-$C_4$ alkyl groups, and
$X^-$ is an anion chosen from halides, phosphates, acetates, lactates, alkyl sulfates, alkyl sulfonates, and alkylaryl sulfonates;
C) diquaternary ammonium salts of formula (VI):

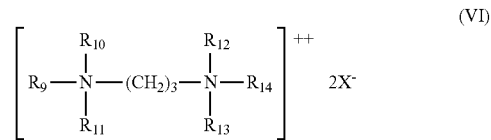

in which:
$R_9$ is chosen from aliphatic groups comprising from 16 to 30 carbon atoms,
$R_{10}$, $R_{11}$, $R_{12}$, $R_{13}$ and $R_{14}$, which may be identical or different, are each chosen from a hydrogen atom and alkyl groups comprising from 1 to 4 carbon atoms, and
$X^-$ is an anion chosen from halides, acetates, phosphates, nitrates and methyl sulfates; and
D) quaternary ammonium salts comprising at least one ester function chosen from said quaternary ammonium salts of formula (VII):

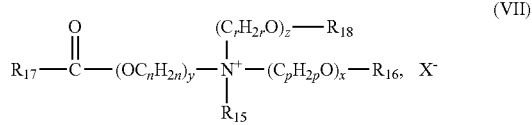

in which:
$R_{15}$ is chosen from $C_1$-$C_6$ alkyl groups, $C_1$-$C_6$ hydroxyalkyl groups and $C_1$-$C_6$ dihydroxyalkyl groups;
$R_{16}$ is chosen from:
acyl groups of the following formula:

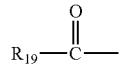

wherein $R_{19}$ is chosen from:
linear and branched, saturated and unsaturated, $C_1$-$C_{22}$ hydrocarbon-based groups, and
a hydrogen atom;

$R_{18}$ is chosen from:
acyl groups of the following formula:

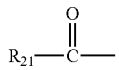

wherein $R_{21}$ is chosen from:
linear and branched, saturated and unsaturated, $C_1$-$C_6$ hydrocarbon-based groups, and
a hydrogen atom;
$R_{17}$, $R_{18}$ and $R_{21}$, which may be identical or different, are each chosen from linear and branched, saturated and unsaturated, $C_7$-$C_{21}$ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network,
with the proviso that the nanoemulsion does not comprise aminosilicone.

62. A composition for caring for a keratin material chosen from body skin, facial skin, mucous membranes, the scalp, the hair, the nails, the eyelashes, and the eyebrows comprising a nanoemulsion comprising:
a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and
at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

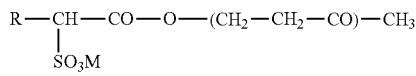

in which R, which may be identical or different in embodiments wherein more than one of said alkylsulfonic derivative is used is chosen from $C_{16}$-$C_{22}$ alkyl groups, and M is chosen from alkali metals and alkaline-earth metals,
wherein the at least one cationic amphiphilic lipid chosen from:
A) quaternary ammonium salts of formula (IV):

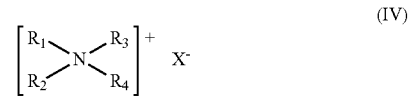

in which:
$R_1$, $R_2$, $R_3$ and $R_4$, which may be identical or different, are each chosen from:
linear and branched aliphatic groups comprising from 1 to 30 carbon atoms and optionally comprising atoms chosen from hetero and halogen atoms, and
aromatic groups, and
$X^-$ is an anion chosen from halides, phosphates, acetates, lactates, ($C_2$-$C_6$)alkyl sulfates, alkyl sulfonates, and alkylaryl sulfonates;
B) quaternary ammonium salts of imidazolinium of formula (V):

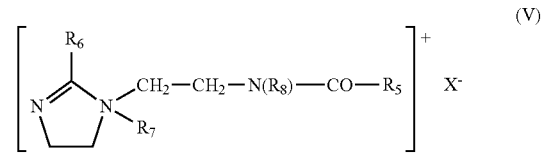

in which:
$R_5$ is chosen from alkenyl and alkyl groups comprising from 8 to 30 carbon atoms,
$R_6$ is chosen from a hydrogen atom, $C_1$-$C_4$ alkyl groups, and alkenyl and alkyl groups comprising from 8 to 30 carbon atoms,
$R_7$ is chosen from $C_1$-$C_4$ alkyl groups,
$R_8$ is chosen from a hydrogen atom and $C_1$-$C_4$ alkyl groups, and
$X^-$ is an anion chosen from halides, phosphates, acetates, lactates, alkyl sulfates, alkyl sulfonates, and alkylaryl sulfonates;
C) diquaternary ammonium salts of formula (VI):

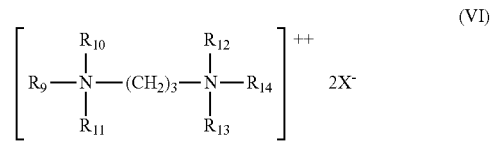

in which:
$R_9$ is chosen from aliphatic groups comprising from 16 to 30 carbon atoms,
$R_{10}$, $R_{11}$, $R_{12}$, $R_{13}$ and $R_{14}$, which may be identical or different, are each chosen from a hydrogen atom and alkyl groups comprising from 1 to 4 carbon atoms, and
$X^-$ is an anion chosen from halides, acetates, phosphates, nitrates and methyl sulfates; and D) quaternary ammonium salts comprising at least one ester function chosen from said quaternary ammonium salts of formula (VII):

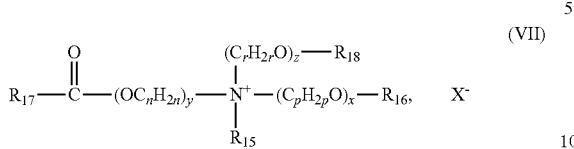

in which:
$R_{15}$ is chosen from $C_1$-$C_6$ alkyl groups, $C_1$-$C_6$ hydroxyalkyl groups and $C_1$-$C_6$ dihydroxyalkyl groups;
$R_{16}$ is chosen from:
acyl groups of the following formula:

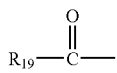

wherein $R_{19}$ is chosen from:
linear and branched, saturated and unsaturated, $C_1$-$C_{22}$ hydrocarbon-based groups, and
a hydrogen atom;
$R_{18}$ is chosen from:
acyl groups of the following formula:

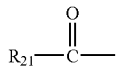

wherein $R_{21}$ is chosen from:
linear and branched, saturated and unsaturated, $C_1$-$C_6$ hydrocarbon-based groups, and
a hydrogen atom;
$R_{17}$, $R_{19}$ and $R_{21}$, which may be identical or different, are each chosen from linear and branched, saturated and unsaturated, $C_7$-$C_{21}$ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network,
with the proviso that the nanoemulsion does not comprise aminosilicone.

63. A composition for washing a keratin material chosen from body skin, facial skin, mucous membranes, the scalp, the hair, the nails, the eyelashes, and the eyebrows comprising a nanoemulsion comprising:
a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and
at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

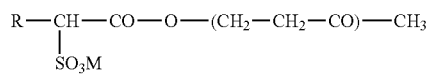

in which R, which may be identical or different in embodiments wherein more than one of said alkylsulfonic derivative is used, is chosen from $C_{16}$-$C_{22}$ alkyl groups, and M is chosen from alkali metals and alkaline-earth metals,
wherein the at least one cationic amphiphilic lipid chosen from:
A) quaternary ammonium salts of formula (IV):

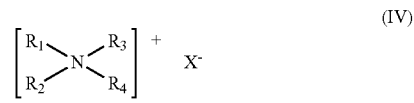

in which:
$R_1$, $R_2$, $R_3$ and $R_4$, which may be identical or different, are each chosen from:
linear and branched aliphatic groups comprising from 1 to 30 carbon atoms and optionally comprising atoms chosen from hetero and halogen atoms, and
aromatic groups, and
$X^-$ is an anion chosen from halides, phosphates, acetates, lactates, ($C_2$-$C_6$)alkyl sulfates, alkyl sulfonates, and alkylaryl sulfonates;
B) quaternary ammonium salts of imidazolinium of formula (V):

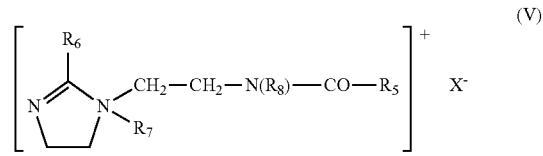

in which:
$R_5$ is chosen from alkenyl and alkyl groups comprising from 8 to 30 carbon atoms, $R_6$ is chosen from a hydrogen atom, $C_1$-$C_4$ alkyl groups, and alkenyl and alkyl groups comprising from 8 to 30 carbon atoms, $R_7$ is chosen from $C_1$-$C_4$ alkyl groups, $R_8$ is chosen from a hydrogen atom and $C_1$-$C_4$ alkyl groups, and $X^-$ is an anion chosen from halides, phosphates, acetates, lactates, alkyl sulfates, alkyl sulfonates, and alkylaryl sulfonates;

C) diquaternary ammonium salts of formula (VI):

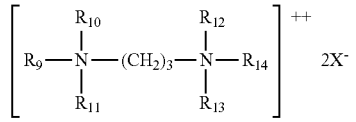

(VI)

in which:

$R_9$ is chosen from aliphatic groups comprising from 16 to 30 carbon atoms, $R_{10}$, $R_{11}$, $R_{12}$, $R_{13}$ and $R_{14}$, which may be identical or different, are each chosen from a hydrogen atom and alkyl groups comprising from 1 to 4 carbon atoms, and $X^-$ is an anion chosen from halides, acetates, phosphates, nitrates and methyl sulfates; and D) quaternary ammonium salts comprising at least one ester function chosen from said quaternary ammonium salts of formula (VII):

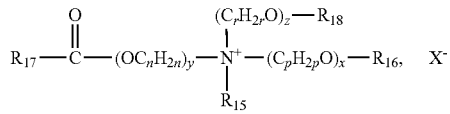

(VII)

in which:

$R_{15}$ is chosen from $C_1$-$C_6$ alkyl groups, $C_1$-$C_6$ hydroxyalkyl groups and $C_1$-$C_6$ dihydroxyalkyl groups;

$R_{16}$ is chosen from:
acyl groups of the following formula:

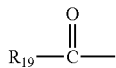

wherein $R_{19}$ is chosen from:
linear and branched, saturated and unsaturated, $C_1$-$C_{22}$ hydrocarbon-based groups, and
a hydrogen atom;

$R_{18}$ is chosen from:
acyl groups of the following formula:

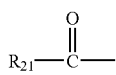

wherein $R_{21}$ is chosen from:
linear and branched, saturated and unsaturated, $C_1$-$C_6$ hydrocarbon-based groups, and
a hydrogen atom;

$R_{17}$, $R_{19}$ and $R_{21}$, which may be identical or different, are each chosen from linear and branched, saturated and unsaturated, $C_7$-$C_{21}$ hydrocarbon-based groups;

n, p and r, which may be identical or different, are each chosen from integers ranging from 2 to 6;

y is chosen from integers ranging from 1 to 10;

x and z, which may be identical or different, are each chosen from integers ranging from 0 to 10;

$X^-$ is chosen from simple and complex, organic and inorganic anions; and provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{19}$ is chosen from linear and branched, saturated and unsaturated, $C_1$-$C_6$ hydrocarbon-based groups, wherein said network is formed by the interaction of said at least one hydrophobic block of the at least one nonionic polymer and said at least one oil, and wherein said nanoemulsion is more viscous than an oil-in-water nanoemulsion lacking such network, with the proviso that the nanoemulsion does not comprise aminosilicone.

64. A cosmetic make up composition for a keratin material chosen from body skin, facial skin, mucous membranes, the scalp, the hair, the nails, the eyelashes, and the eyebrows comprising a nanoemulsion comprising:

a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

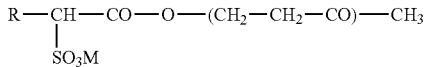

in which R, which may be identical or different in embodiments wherein more than one of said alkylsulfonic derivative is used is chosen from $C_{16}$-$C_{22}$ alkyl groups, and M is chosen from alkali metals and alkaline-earth metals, wherein the at least one cationic amphiphilic lipid chosen from:

A) quaternary ammonium salts of formula (IV):

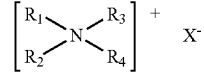

(IV)

in which:
R₁, R₂, R₃ and R₄, which may be identical or different, are each chosen from:
  linear and branched aliphatic groups comprising from 1 to 30 carbon atoms and optionally comprising atoms chosen from hetero and halogen atoms, and
  aromatic groups, and
X⁻ is an anion chosen from halides, phosphates, acetates, lactates, (C₂-C₆)alkyl sulfates, alkyl sulfonates, and alkylaryl sulfonates;
B) quaternary ammonium salts of imidazolinium of formula (V):

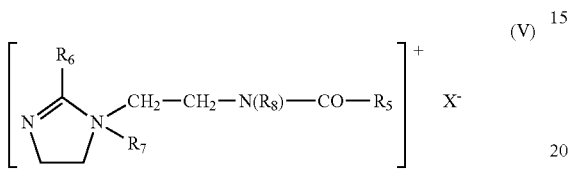

in which:
R₅ is chosen from alkenyl and alkyl groups comprising from 8 to 30 carbon atoms,
R₆ is chosen from a hydrogen atom, C₁-C₄ alkyl groups, and alkenyl and alkyl groups comprising from 8 to 30 carbon atoms,
R₇ is chosen from C₁-C₄ alkyl groups,
R₈ is chosen from a hydrogen atom and C₁-C₄ alkyl groups, and
X⁻ is an anion chosen from halides, phosphates, acetates, lactates, alkyl sulfates, alkyl sulfonates, and alkylaryl sulfonates;
C) diquaternary ammonium salts of formula (VI):

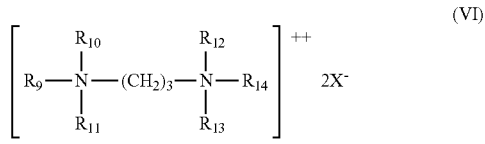

in which:
R₉ is chosen from aliphatic groups comprising from 16 to 30 carbon atoms,
R₁₀, R₁₁, R₁₂, R₁₃ and R₁₄, which may be identical or different, are each chosen from a hydrogen atom and alkyl groups comprising from 1 to 4 carbon atoms, and
X⁻ is an anion chosen from halides, acetates, phosphates, nitrates and methyl sulfates; and
D) quaternary ammonium salts comprising at least one ester function chosen from said quaternary ammonium salts of formula (VII):

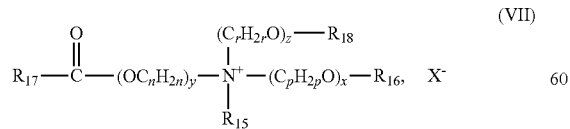

in which:
R₁₅ is chosen from C₁-C₆ alkyl groups, C₁-C₆ hydroxyalkyl groups and C₁-C₆ dihydroxyalkyl groups;
R₁₆ is chosen from:
  acyl groups of the following formula:

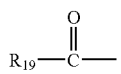

wherein R₁₉ is chosen from:
    linear and branched, saturated and unsaturated, C₁-C₂₂ hydrocarbon-based groups, and
    a hydrogen atom;
R₁₈ is chosen from:
  acyl groups of the following formula:

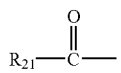

wherein R₂₁ is chosen from:
    linear and branched, saturated and unsaturated, C₁-C₆ hydrocarbon-based groups, and
    a hydrogen atom;
R₁₇, R₁₉ and R₂₁, which may be identical or different, are each chosen from linear and branched, saturated and unsaturated, C₇-C₂₁ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
X⁻ is chosen from simple and complex, organic and inorganic anions; and
provided that the sum x+y+z is from 1 to 15, and that when x is 0, then R₁₆ is chosen from linear and branched, saturated and unsaturated, C₁-C₂₂ hydrocarbon-based groups, and that when z is 0, then R₁₈ is chosen from linear and branched, saturated and unsaturated, C₁-C₆ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network,
with the proviso that the nanoemulsion does not comprise amino silicone.

65. A cosmetic make-up-removing composition for a keratin material chosen from body skin, facial skin, mucous membranes, the scalp, the hair, the nails, the eyelashes, and the eyebrows comprising a nanoemulsion comprising:
a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and
at least one ionic amphiphilic lipid chosen from cationic amphiphilic lipids and anionic amphiphilic lipids chosen from:
  alkaline salts of dicetyl phosphate and of dimyristyl phosphate;
  alkaline salts of cholesteryl sulfate;
  alkaline salts of cholesteryl phosphate;
  lipoamino acids and salts thereof;
  sodium salts of phosphatidic acid;
  phospholipids; and alkylsulfonic derivatives of formula:

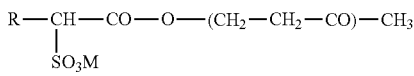

in which R, which may be identical or different in embodiments wherein more than one of said alkylsulfonic derivative is used is chosen from $C_{16}$-$C_{22}$ alkyl groups, and M is chosen from alkali metals and alkaline-earth metals, wherein the at least one cationic amphiphilic lipid chosen from:

A) quaternary ammonium salts of formula (IV):

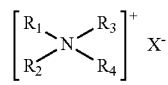

(IV)

in which:
$R_1$, $R_2$, $R_3$ and $R_4$, which may be identical or different, are each chosen from:
  linear and branched aliphatic groups comprising from 1 to 30 carbon atoms and optionally comprising atoms chosen from hetero and halogen atoms, and
  aromatic groups, and
$X^-$ is an anion chosen from halides, phosphates, acetates, lactates, ($C_2$-$C_6$)alkyl sulfates, alkyl sulfonates, and alkylaryl sulfonates;

B) quaternary ammonium salts of imidazolinium of formula (V):

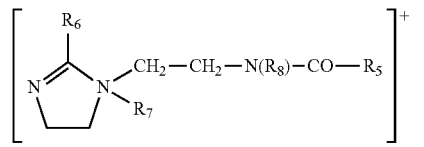

(V)

in which:
$R_5$ is chosen from alkenyl and alkyl groups comprising from 8 to 30 carbon atoms,
$R_6$ is chosen from a hydrogen atom, $C_1$-$C_4$ alkyl groups, and alkenyl and alkyl groups comprising from 8 to 30 carbon atoms,
$R_7$ is chosen from $C_1$-$C_4$ alkyl groups,
$R_8$ is chosen from a hydrogen atom and $C_1$-$C_4$ alkyl groups, and
$X^-$ is an anion chosen from halides, phosphates, acetates, lactates, alkyl sulfates, alkyl sulfonates, and alkylaryl sulfonates;

C) diquaternary ammonium salts of formula (VI):

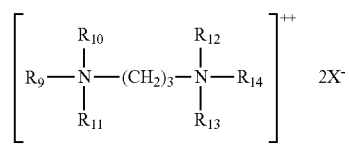

(VI)

in which:
$R_9$ is chosen from aliphatic groups comprising from 16 to 30 carbon atoms,
$R_{10}$, $R_{11}$, $R_{12}$, $R_{13}$ and $R_{14}$, which may be identical or different, are each chosen from a hydrogen atom and alkyl groups comprising from 1 to 4 carbon atoms, and
$X^-$ is an anion chosen from halides, acetates, phosphates, nitrates and methyl sulfates; and D) quaternary ammonium salts comprising at least one ester function chosen from said quaternary ammonium salts of formula (VII):

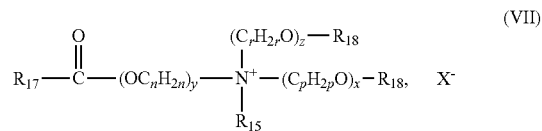

(VII)

in which:
$R_{15}$ is chosen from $C_1$-$C_6$ alkyl groups, $C_1$-$C_6$ hydroxyalkyl groups and $C_1$-$C_6$ dihydroxyalkyl groups;
$R_{16}$ is chosen from:
  acyl groups of the following formula:

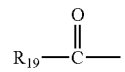

wherein $R_{19}$ is chosen from:
    linear and branched, saturated and unsaturated, $C_1$-$C_{22}$ hydrocarbon-based groups, and
    a hydrogen atom;
$R_{18}$ is chosen from:
  acyl groups of the following formula:

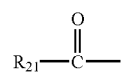

wherein $R_{21}$ is chosen from:
    linear and branched, saturated and unsaturated, $C_1$-$C_6$ hydrocarbon-based groups, and
    a hydrogen atom;
$R_{17}$, $R_{19}$ and $R_{21}$, which may be identical or different, are each chosen from linear and branched, saturated and unsaturated, $C_7$-$C_{21}$ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network, with the proviso that the nanoemulsion does not comprise aminosilicone.

66. A non-therapeutic care process for a keratin material comprising applying to said keratin material a nanoemulsion comprising:
a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and
at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

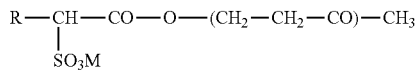

in which R, which may be identical or different in embodiments wherein more than one of said alkylsulfonic derivative is used is chosen from $C_{16}$-$C_{22}$ alkyl groups and M is chosen from alkali metals and alkaline-earth metals,
wherein the at least one cationic amphiphilic lipid chosen from:
A) quaternary ammonium salts of formula (IV):

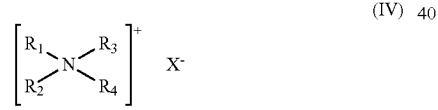

in which:
$R_1$, $R_2$, $R_3$ and $R_4$, which may be identical or different, are each chosen from:
linear and branched aliphatic groups comprising from 1 to 30 carbon atoms and optionally comprising atoms chosen from hetero and halogen atoms, and
aromatic groups, and
$X^-$ is an anion chosen from halides, phosphates, acetates, lactates, ($C_2$-$C_6$)alkyl sulfates, alkyl sulfonates, and alkylaryl sulfonates;
B) quaternary ammonium salts of imidazolinium of formula (V):

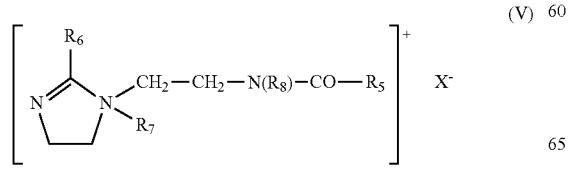

in which:
$R_5$ is chosen from alkenyl and alkyl groups comprising from 8 to 30 carbon atoms,
$R_6$ is chosen from a hydrogen atom, $C_1$-$C_4$ alkyl groups, and alkenyl and alkyl groups comprising from 8 to 30 carbon atoms,
$R_7$ is chosen from $C_1$-$C_4$ alkyl groups,
$R_8$ is chosen from a hydrogen atom and $C_1$-$C_4$ alkyl groups, and
$X^-$ is an anion chosen from halides, phosphates, acetates, lactates, alkyl sulfates, alkyl sulfonates, and alkylaryl sulfonates;
C) diquaternary ammonium salts of formula (VI):

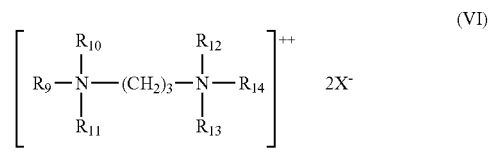

in which:
$R_9$ is chosen from aliphatic groups comprising from 16 to 30 carbon atoms,
$R_{10}$, $R_{11}$, $R_{12}$, $R_{13}$ and $R_{14}$, which may be identical or different, are each chosen from a hydrogen atom and alkyl groups comprising from 1 to 4 carbon atoms, and
$X^-$ is an anion chosen from halides, acetates, phosphates, nitrates and methyl sulfates; and
D) quaternary ammonium salts comprising at least one ester function chosen from said quaternary ammonium salts of formula (VII):

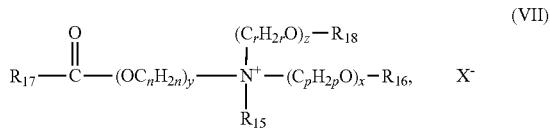

in which:
$R_{15}$ is chosen from $C_1$-$C_6$ alkyl groups, $C_1$-$C_6$ hydroxyalkyl groups and $C_1$-$C_6$ dihydroxyalkyl groups;
$R_{16}$ is chosen from:
acyl groups of the following formula:

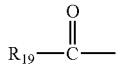

wherein $R_{19}$ is chosen from:
linear and branched, saturated and unsaturated, $C_1$-$C_{22}$ hydrocarbon-based groups, and
a hydrogen atom;
$R_{18}$ is chosen from:
acyl groups of the following formula:

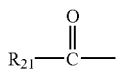

wherein $R_{21}$ is chosen from:
linear and branched, saturated and unsaturated, $C_1$-$C_6$ hydrocarbon-based groups, and
a hydrogen atom;
$R_{17}$, $R_{19}$ and $R_{21}$, which may be identical or different, are each chosen from linear and branched, saturated and unsaturated, $C_7$-$C_{21}$ hydrocarbon-based groups;

n, p and r, which may be identical or different, are each chosen from integers ranging from 2 to 6;

y is chosen from integers ranging from 1 to 10;

x and z, which may be identical or different, are each chosen from integers ranging from 0 to 10;

$X^-$ is chosen from simple and complex, organic and inorganic anions; and provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups, wherein said network is formed by the interaction of said at least one hydrophobic block of the at least one nonionic polymer and said at least one oil, and wherein said nanoemulsion is more viscous than an oil-in-water nanoemulsion lacking such network, with the proviso that the nanoemulsion does not comprise aminosilicone.

67. A process according to claim 66, wherein said keratin material is chosen from the skin, the hair, the eyelashes, the eyebrows, the nails, mucous membranes and the scalp.

68. A non-therapeutic care process for a keratin material comprising applying to said keratin material a composition for topical use chosen from cosmetic compositions and dermopharmaceutical compositions, wherein said composition for topical use comprises a nanoemulsion comprising:

a network of oil globules with an average size of less than 150 nm comprising at least one oil, at least one amphiphilic lipid, and at least one nonionic polymer, wherein said at least one nonionic polymer is chosen from polyether-polyurethanes comprising in their chain at least one polyoxyethylenated hydrophilic block and at least one hydrophobic block chosen from aliphatic chains, cycloaliphatic chains, and aromatic chains, and at least one ionic amphiphilic lipid chosen from cationic amphiphilic lipids and anionic amphiphilic lipids chosen from:

alkaline salts of dicetyl phosphate and of dimyristyl phosphate;

alkaline salts of cholesteryl sulfate;

alkaline salts of cholesteryl phosphate;

lipoamino acids and salts thereof;

sodium salts of phosphatidic acid;

phospholipids; and alkylsulfonic derivatives of formula:

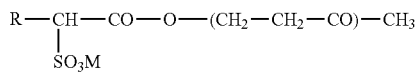

in which R, which may be identical or different in embodiments wherein more than one of said alkylsulfonic derivative is used is chosen from $C_{16}$-$C_{22}$ alkyl groups, and M is chosen from alkali metals and alkaline-earth metals, wherein the at least one cationic amphiphilic lipid chosen from:

A) quaternary ammonium salts of formula (IV):

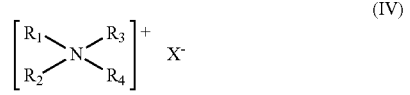

in which:

$R_1$, $R_2$, $R_3$ and $R_4$, which may be identical or different, are each chosen from:

linear and branched aliphatic groups comprising from 1 to 30 carbon atoms and optionally comprising atoms chosen from hetero and halogen atoms, and aromatic groups, and $X^-$ is an anion chosen from halides, phosphates, acetates, lactates, ($C_2$-$C_6$)alkyl sulfates, alkyl sulfonates, and alkylaryl sulfonates;

B) quaternary ammonium salts of imidazolinium of formula (V):

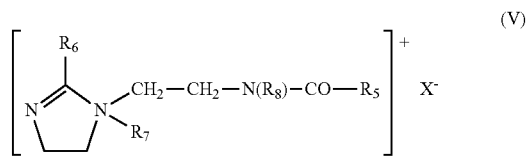

in which:

$R_5$ is chosen from alkenyl and alkyl groups comprising from 8 to 30 carbon atoms, $R_6$ is chosen from a hydrogen atom, $C_1$-$C_4$ alkyl groups, and alkenyl and alkyl groups comprising from 8 to 30 carbon atoms, $R_7$ is chosen from $C_1$-$C_4$ alkyl groups, $R_8$ is chosen from a hydrogen atom and $C_1$-$C_4$ alkyl groups, and $X^-$ is an anion chosen from halides, phosphates, acetates, lactates, alkyl sulfates, alkyl sulfonates, and alkylaryl sulfonates;

C) diquaternary ammonium salts of formula (VI):

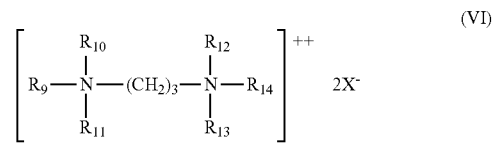

in which:

$R_9$ is chosen from aliphatic groups comprising from 16 to 30 carbon atoms, $R_{10}$, $R_{11}$, $R_{12}$, $R_{13}$ and $R_{14}$, which may be identical or different, are each chosen from a hydrogen atom and alkyl groups comprising from 1 to 4 carbon atoms, and $X^-$ is an anion chosen from halides, acetates, phosphates, nitrates and methyl sulfates; and D) quaternary ammonium salts comprising at least one ester function chosen from said quaternary ammonium salts of formula (VII):

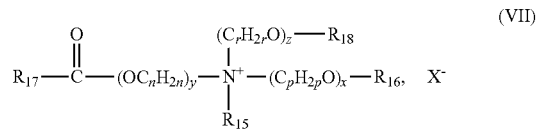

in which:

$R_{15}$ is chosen from $C_1$-$C_6$ alkyl groups, $C_1$-$C_6$ hydroxyalkyl groups and $C_1$-$C_6$ dihydroxyalkyl groups;

$R_{16}$ is chosen from:
acyl groups of the following formula:

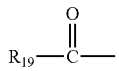

wherein $R_{19}$ is chosen from:
linear and branched, saturated and unsaturated, $C_1$-$C_{22}$ hydrocarbon-based groups, and
a hydrogen atom;
$R_{18}$ is chosen from:
acyl groups of the following formula:

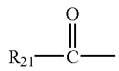

wherein $R_{21}$ is chosen from:
linear and branched, saturated and unsaturated, $C_1$-$C_6$ hydrocarbon-based groups, and
a hydrogen atom;
$R_{17}$, $R_{19}$ and $R_{21}$, which may be identical or different, are each chosen from linear and branched, saturated and unsaturated, $C_7$-$C_{21}$ hydrocarbon-based groups;
n, p and r, which may be identical or different, are each chosen from integers ranging from 2 to 6;
y is chosen from integers ranging from 1 to 10;
x and z, which may be identical or different, are each chosen from integers ranging from 0 to 10;
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups,
wherein said network is formed by the interaction of said at least one hydrophobic block of the at least one nonionic polymer and said at least one oil, and
wherein said nanoemulsion is more viscous than an oil-in-water nanoemulsion lacking such network,
with the proviso that the nanoemulsion does not comprise aminosilicone.

69. A process according to claim 68, wherein said keratin material is chosen from the skin, the hair, the eyelashes, the eyebrows, the nails, mucous membranes and the scalp.

70. A process for thickening oil-in-water nanoemulsions comprising including at least one nonionic polymer, wherein said at least one nonionic polymer is chosen from polyetherpolyurethanes comprising in their chain at least one polyoxyethylenated hydrophilic block and at least one hydrophobic block chosen from aliphatic chains, cycloaliphatic chains, and aromatic chains, in said nanoemulsions comprising:
a network of oil globules with an average size of less than 150 nm comprising at least one oil, at least one amphiphilic lipid, and at least one nonionic polymer, and
at least one ionic amphiphilic lipid chosen from cationic amphiphilic lipids and anionic amphiphilic lipids chosen from:
alkaline salts of dicetyl phosphate and of dimyristyl phosphate;
alkaline salts of cholesteryl sulfate;
alkaline salts of cholesteryl phosphate;
lipoamino acids and salts thereof;
sodium salts of phosphatidic acid;
phospholipids; and
alkylsulfonic derivatives of formula:

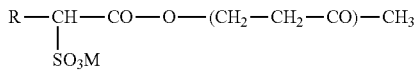

in which R, which may be identical or different in embodiments wherein more than one of said alkylsulfonic derivative is used, is chosen from $C_{16}$-$C_{22}$ alkyl groups, and M is chosen from alkali metals and alkaline-earth metals,
wherein the at least one cationic amphiphilic lipid chosen from:
A) quaternary ammonium salts of formula (IV):

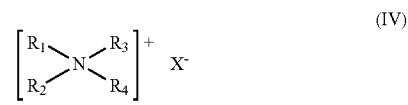

in which:
$R_1$, $R_2$, $R_3$ and $R_4$, which may be identical or different, are each chosen from:
linear and branched aliphatic groups comprising from 1 to 30 carbon atoms and optionally comprising atoms chosen from hetero and halogen atoms, and
aromatic groups, and
$X^-$ is an anion chosen from halides, phosphates, acetates, lactates, ($C_2$-$C_6$)alkyl sulfates, alkyl sulfonates, and alkylaryl sulfonates;
B) quaternary ammonium salts of imidazolinium of formula (V):

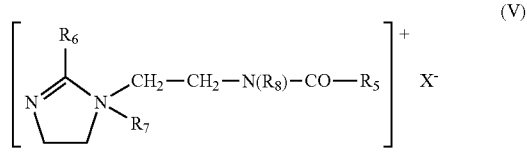

in which:
$R_5$ is chosen from alkenyl and alkyl groups comprising from 8 to 30 carbon atoms,
$R_6$ is chosen from a hydrogen atom, $C_1$-$C_4$ alkyl groups, and alkenyl and alkyl groups comprising from 8 to 30 carbon atoms,
$R_7$ is chosen from $C_1$-$C_4$ alkyl groups,
$R_8$ is chosen from a hydrogen atom and $C_1$-$C_4$ alkyl groups, and
$X^-$ is an anion chosen from halides, phosphates, acetates, lactates, alkyl sulfates, alkyl sulfonates, and alkylaryl sulfonates;

C) diquaternary ammonium salts of formula (VI):

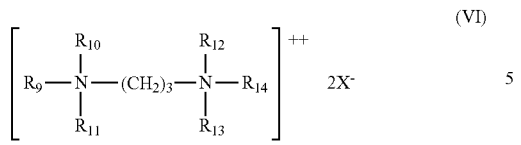

in which:

$R_9$ is chosen from aliphatic groups comprising from 16 to 30 carbon atoms, $R_{10}$, $R_{11}$, $R_{12}$, $R_{13}$ and $R_{14}$, which may be identical or different, are each chosen from a hydrogen atom and alkyl groups comprising from 1 to 4 carbon atoms, and $X^-$ is an anion chosen from halides, acetates, phosphates, nitrates and methyl sulfates; and D) quaternary ammonium salts comprising at least one ester function chosen from said quaternary ammonium salts of formula (VII):

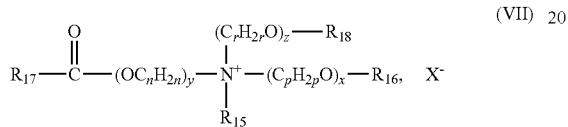

in which:

$R_{15}$ is chosen from $C_1$-$C_6$ alkyl groups, $C_1$-$C_6$ hydroxyalkyl groups and $C_1$-$C_6$ dihydroxyalkyl groups;

$R_{16}$ is chosen from:
  acyl groups of the following formula:

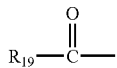

wherein $R_{19}$ is chosen from:
    linear and branched, saturated and unsaturated, $C_1$-$C_{22}$ hydrocarbon-based groups, and
    a hydrogen atom;

$R_{18}$ is chosen from:
  acyl groups of the following formula:

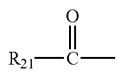

wherein $R_{21}$ is chosen from:
    linear and branched, saturated and unsaturated, $C_1$-$C_6$ hydrocarbon-based groups, and
    a hydrogen atom;

$R_{17}$, $R_{19}$ and $R_{21}$, which may be identical or different, are each chosen from linear and branched, saturated and unsaturated, $C_7$-$C_{21}$ hydrocarbon-based groups;

n, p and r, which may be identical or different, are each chosen from integers ranging from 2 to 6;

y is chosen from integers ranging from 1 to 10;

x and z, which may be identical or different, are each chosen from integers ranging from 0 to 10;

$X^-$ is chosen from simple and complex, organic and inorganic anions; and provided that the sum x+y+z is from 1 to 15, and that when x is 0, then $R_{16}$ is chosen from linear and branched, saturated and unsaturated, $C_1$-$C_{22}$ hydrocarbon-based groups, and that when z is 0, then $R_{18}$ is chosen from linear and branched, saturated and unsaturated, $C_1$-$C_6$ hydrocarbon-based groups, wherein said network is formed by the interaction of said at least one hydrophobic block of the at least one nonionic polymer and said at least one oil, and wherein said nanoemulsion is more viscous than an oil-in-water nanoemulsion lacking such network, with the proviso that said nanoemulsion does not comprise aminosilicone.

71. A nanoemulsion according to claim 2, wherein said weight ratio ranges from 1.2:1 to 10:1.

72. A nanoemulsion according to claim 2, wherein said weight ratio ranges from 1.5:1 to 6:1.

73. A nanoemulsion according to claim 2, wherein said weight ratio ranges from 2:1 to 5:1.

74. A nanoemulsion according to claim 49, wherein said anions derived from organic acids are chosen from acetate and lactate.

* * * * *

UNITED STATES PATENT AND TRADEMARK OFFICE
CERTIFICATE OF CORRECTION

PATENT NO. : 8,114,389 B2
APPLICATION NO. : 11/097371
DATED : February 14, 2012
INVENTOR(S) : Veronique Douin et al.

It is certified that error appears in the above-identified patent and that said Letters Patent is hereby corrected as shown below:

Claim 1, col. 29, line 21, "$R_{21}$ chosen from" should read -- $R_{21}$ is chosen from --.

Claim 61, col. 35, line 13, "$R_{18}$" should read -- $R_{19}$ --.

Claim 63, col. 40, line 13, "then R19 is" should read -- then $R_{18}$ is --.

Signed and Sealed this
Nineteenth Day of June, 2012

David J. Kappos
*Director of the United States Patent and Trademark Office*